(12) United States Patent
Takahashi

(10) Patent No.: US 11,006,834 B2
(45) Date of Patent: May 18, 2021

(54) INFORMATION PROCESSING DEVICE AND INFORMATION PROCESSING METHOD

(71) Applicant: SONY CORPORATION, Tokyo (JP)

(72) Inventor: Shuichi Takahashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 19 days.

(21) Appl. No.: 16/337,478

(22) PCT Filed: Oct. 23, 2017

(86) PCT No.: PCT/JP2017/038212
§ 371 (c)(1),
(2) Date: Mar. 28, 2019

(87) PCT Pub. No.: WO2018/088186
PCT Pub. Date: May 17, 2018

(65) Prior Publication Data
US 2019/0254525 A1    Aug. 22, 2019

(30) Foreign Application Priority Data

Nov. 8, 2016 (JP) .............................. JP2016-217804

(51) Int. Cl.
*A61B 5/00* (2006.01)
*G06N 20/00* (2019.01)
(Continued)

(52) U.S. Cl.
CPC ............ *A61B 5/0042* (2013.01); *A61B 5/378* (2021.01); *A61B 5/4064* (2013.01);
(Continued)

(58) Field of Classification Search
CPC . A61B 5/0042; A61B 5/04842; A61B 5/7267; A61B 5/4064; G06F 16/00;
(Continued)

(56) References Cited

U.S. PATENT DOCUMENTS

2011/0319784 A1    12/2011    Nakagawa
2013/0274586 A1    10/2013    Miyazaki et al.

FOREIGN PATENT DOCUMENTS

EP    2649935 A1    10/2013
JP    2003-058298 A    2/2003
(Continued)

OTHER PUBLICATIONS

Bosse et al., Neurophysiological assessment of perceived image quality using steady-state visual evoked potentials, Sep. 2015, Proceedings of SPIE Optical Engineering, vol. 9599, pp. 14-1 to 14-12 (Year: 2015).*

(Continued)

*Primary Examiner* — Said M Elnoubi
(74) *Attorney, Agent, or Firm* — Chip Law Group

(57) ABSTRACT

An assessment model for enabling a subjective assessment value to be estimated from a brainwave feature amount is constructed, and assessment data which does not deviate from a subjective assessment result on the basis of an objective brainwave signal by using the assessment model can be acquired. An assessment model representing relevance between a brainwave feature amount of a subject and a subjective assessment value of the subject with respect to a stimulus is constructed by presenting the stimulus to the subject. For example, images with different image qualities and a standard image are alternately displayed on a display unit which is a stimulus presentation unit, brainwave feature amount corresponding to an image quality of a subject observing the displayed images and subjective assessment values corresponding to image qualities are acquired, and an image quality assessment model for enabling subjective assessment values to be estimated from the brainwave feature amounts is constructed by machine learning in which (Continued)

the brainwave feature amounts and the subjective assessment values are used as input data.

18 Claims, 22 Drawing Sheets

(51) Int. Cl.

| | | |
|---|---|---|
| *G06T 5/00* | (2006.01) | |
| *G06T 5/20* | (2006.01) | |
| *G06T 7/00* | (2017.01) | |
| *G06F 16/00* | (2019.01) | |
| *G06F 3/01* | (2006.01) | |
| *A61B 5/378* | (2021.01) | |

(52) U.S. Cl.
CPC .............. *A61B 5/7267* (2013.01); *G06F 3/01* (2013.01); *G06F 16/00* (2019.01); *G06N 20/00* (2019.01); *G06T 5/009* (2013.01); *G06T 5/20* (2013.01); *G06T 7/0012* (2013.01)

(58) Field of Classification Search
CPC .......... G06F 3/01; G06N 20/00; G06N 20/10; G06T 5/009; G06T 5/20; G06T 7/0012; G16H 50/50; G16H 50/20
See application file for complete search history.

(56) References Cited

FOREIGN PATENT DOCUMENTS

| | | |
|---|---|---|
| JP | 2010-057658 A | 3/2010 |
| JP | 2013-233424 A | 11/2013 |
| JP | 2014-021986 A | 2/2014 |
| JP | 2016-072794 A | 5/2016 |
| JP | 2016-146075 A | 8/2016 |
| WO | 2010/093007 A1 | 8/2010 |

OTHER PUBLICATIONS

International Search Report and Written Opinion of PCT Application No. PCT/JP2017/038212, dated Dec. 26, 2017, 09 pages of ISRWO.

Kawakami, et al., "A Note on Image Classification Using EEG Features during Watching Images (4)—Verification of Using Multiple Users' EEG Signals—" ITE Technical Report vol. 30, No. 7, Feb. 22, 2015, pp. 185-190.

Hondo, et al., "Evaluation. of Objective Quality Metric for HDR Images by Subjective Quality Assessment", IEICE Technical Report, vol. 112, No. 475, 23-28 pages.

Hayashi, et al., "Extra High Quality Images Assessment Using EEG Instrumentation and Assessment Words on high Order Sensation", IPSJ SIG Note, vol. 2000, No. 26, Mar. 9, 2000, 25-30 pages.

Moon, et al., "Perceptual Experience Analysis for Tone-mapped HDR Videos Based on EEG and Peripheral Physiological Signals", IEEE Transactions on Autonomous Mental Development, vol. 7, No. 3, Sep. 2015, pp. 236-247.

Bosse, et al., "Neurophysiological Assessment of Perceived Image Quality Using Steady-State Visual Evoked Potentials", Proc. of SPIE vol. 9599, pp. 959914-1 to 959914-12.

Kawakamii, et al., "A Note on Image Classification Using EEG Features during Watching Images (4)—Verification of Using Multiple Users' EEG Signals—", ITE Technical Report, vol. 39, No. 7, Feb. 23, 2015, pp. 185-190.

Hondo, et al., "Evaluation of Objective Quality Metric for HDR Images by Subjective Quality Assessment", IEICE Technical Report, vol. 112, No. 475, Mar. 4, 2013, pp. 23-28.

Hayashi, et al., "Extra High Quality Images Assessment-Using EEG instrumentation and assessment words on High Order Sensation—", Information Processing Society of Japan SIG Notes, vol. 2000, No. 26, Mar. 10, 2003, pp. 25-30.

\* cited by examiner

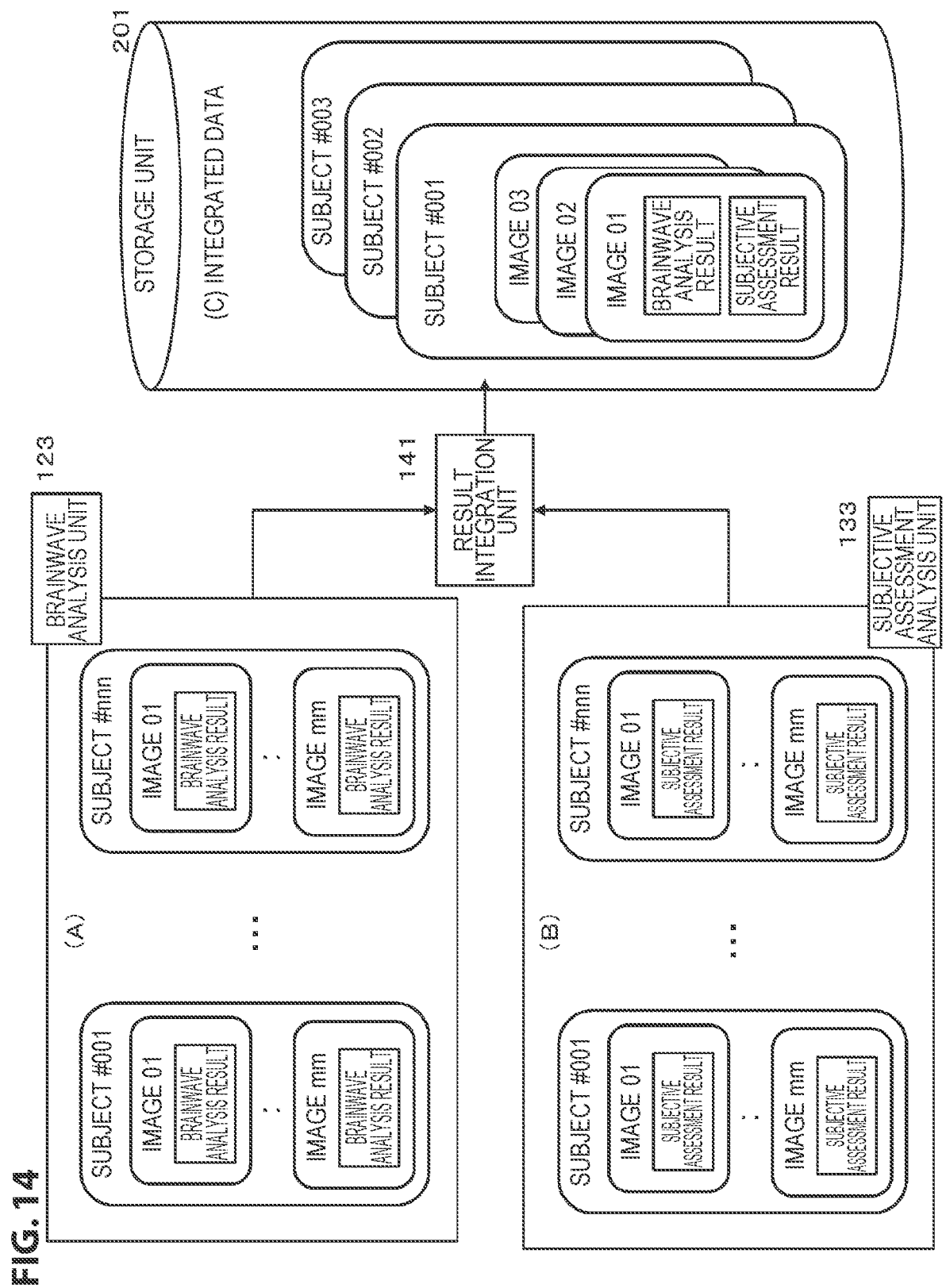

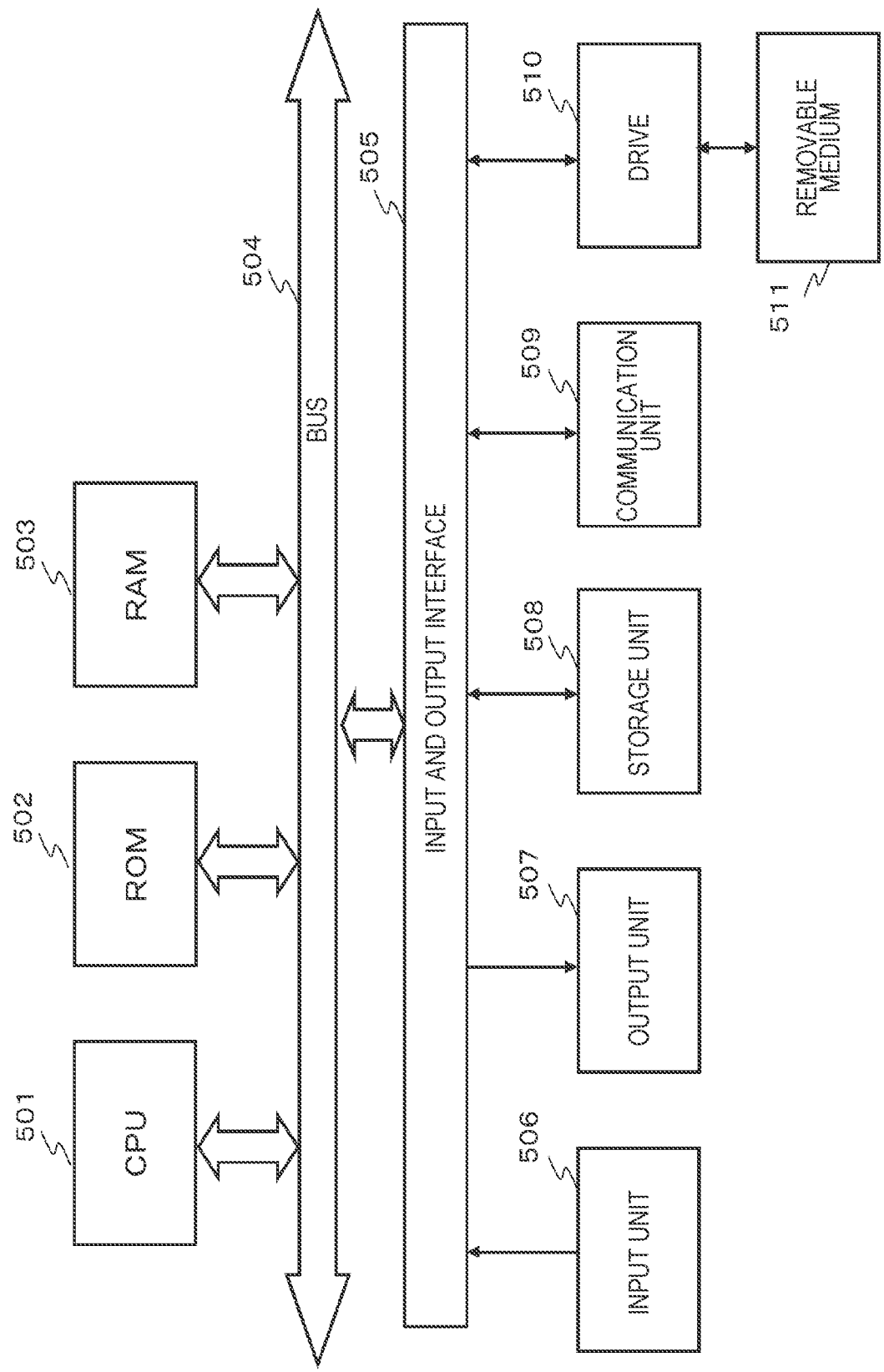

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2017/038212 filed on Oct. 23, 2017, which claims priority benefit of Japanese Patent Application No. JP 2016-217804 filed in the Japan Patent Office on Nov. 8, 2016. Each of the above-referenced applications is hereby incorporated herein by reference in its entirety.

TECHNICAL FIELD

The present disclosure relates to an information processing device, an information processing method, and a program, and more particularly, to an information processing device, an information processing method, and a program capable of executing a process of generating an assessment model for enabling an assessment (subjective assessment) of a user (subject) to a stimulus such as an image to be estimated on the basis of, for example, a brainwave of the user to which the stimulus such as an image presentation process is presented and executing estimation of an assessment value to which the assessment model is applied.

BACKGROUND ART

In recent years, image quality improvement technologies for images have progressed and use of high dynamic range (HDR) images with extended colors or luminance ranges which can be output as delivery content of television broadcast or media recording content such as Blu-ray (registered trademark) discs (BDs) has extended.

Note that an image of the related art with a narrower outputable color or luminance range than an HDR image is referred to as a standard dynamic range (SDR) image.

An HDR image has an outputable color or an outputable luminance range further extended than an SDR image of the related art, and thus a more natural image such as a scene actually seen by eyes of people can be output.

An HDR image has a contrast ratio between a maximum brightness color and a minimum brightness color, for example, 10000:1 or more, and thus an actual world can be realistically expressed.

An HDR image can record almost all of the luminance of a visible range and thus support the same dynamic range and color gamut as human vision properties. An HDR image can be said to be a considerably high-quality image than an image of the related art in terms of realistic expression of shade, expression of glare, or the like.

On the other hand, assessment processes for qualities of images can be classified into an objective assessment process and a subjective assessment process.

The subjective assessment process is a process of sensually assessing whether an image observer determines the quality of an observation target image to be good or bad. The objective assessment process is an assessment process executed by removing such personal subjectivity.

At present, various studies for new image quality improvement of images have been carried out. An improvement in subjective assessment for an image quality is one of the elements to be considered when image quality improvement technologies or compression encoding technologies for images are developed.

As subjective schemes for image quality assessment, for example, there are the following various assessment schemes executed together by experts or non-experts of image processing:

n-stage assessment (MOS: Mean Opinion Score), (where n=5, 7, or the like);

score assessment (magnitude estimation method or the like); and introspective assessment (comment recording).

These schemes are subjective schemes of executing an image quality assessment process by replacing feelings of images viewed by experts or non-experts of image processing with numbers or text.

However, the subjective assessment processes have the following problems:

(1) results are irregular for each individual because of subjective assessment;

(2) since assessment axes are designated, items deviating from the axes are not assessed;

(3) assessment results are considerably influenced by experience or knowledge of subjects; and (4) many subjects are necessary and time and cost are required to guarantee precision of results.

For example, there are the foregoing problems.

To solve the problems, it is necessary to execute image quality assessment objectively.

Here, when an objective assessment result deviates from a subjective assessment result, there is no meaning.

Accordingly, it is important to generate an objective assessment result which does not deviate from a subjective assessment result.

As an objective scheme for image quality assessment, peak signal-to-noise ratio (PSNR) and structured similarity index measure (SSIM) are known.

Both the schemes are schemes of outputting image quality assessment values as objective numerical values.

However, a case in which numerical values obtained as image quality assessment values by the foregoing PSNR and SSIM do not match actual feelings of image viewers is pointed out, and thus subjective assessment is not yet replaced completely.

To solve the problem, a study for an objective assessment scheme for an image quality using brainwaves of image observers has recently been carried out.

The image quality assessment scheme using brainwaves is configured to detect how subjects viewing assessment target images feel by monitoring changes in the brainwaves.

It is considered that a human feeling or a kind of stimulus presented to an image observer can be inferred from a brainwave by linking a brainwave of the image observer which is an objective assessment result with an actual feeling based on a subjective assessment result of the image observer.

However, this scheme has the following problems:

(1) cost and training are necessary to introduce and administrate a device; and (2) this scheme is more complicated than the above-described objective assessment scheme since electrodes are worn on a subject at the present time.

However, it is considered that results which are rarely influenced by knowledge or experience of a subject and assessment axes can be obtained.

In addition, by synchronizing a presentation timing of an image with a recording timing of a brainwave, it is possible to record when and what a subject feels.

As examples of the related art in which image assessment structures using brainwaves are disclosed, for example, there are Patent Literature 1 (JP 2014-021986A), Patent Literature 2 (JP 2003-058298A), Non-Patent Literature 1, and Non-Patent Literature 2.

Patent Literature 1 discloses, for example, a configuration capable of supplying content in accordance with a favorite of users by analyzing relevance between brainwaves of the users observing image content and observing regions of the users and determining preference for content.

Patent Literature 2 discloses a device that classifies subjective knowledge, interests, or the like of a user with respect to viewing targets from brainwaves, in particular, event-related potential (ERP).

On the other hand, Non-Patent Literature 1 is a document related to a study on a steady-state visual evoked potential (SSVEP) measured from brainwaves and reports that subjective qualities of texture images with different compression ratios and feature amounts of SSVEP have high correlation.

In addition, Non-Patent Literature 2 discloses a scheme of assessing an image quality by displaying a low dynamic range (LDR) image which is a low dynamic image and a moving image of a high dynamic range (HDR) which is a tone-mapped high dynamic image on a display which does not correspond to the HDR.

Specifically, the report describes a study to structure a model for discriminating whether a brainwave is obtained as an appreciation result between moving images of an HDR and an SDR by measuring a visual evoked potential from the brainwave of a viewer, further acquiring a subjective assessment of the viewer, and executing machine learning in which a feature amount of VEP is used as a student and a subjective assessment value is used as a supervisor.

CITATION LIST

Patent Literature

Patent Literature 1: JP 2014-021986A
Patent Literature 2: JP 2003-058298A

Non-Patent Literature

Non-Patent Literature 1: Sebastian Bosse, et al, "Neurophysiological assessment of perceived image quality using steady-state visual evoked potentials," SPIE Optical Engineering Applications, International Society for Optics and Photonics (2015)
Non-Patent Literature 2: S. Moon, et al, "Perceptual experience analysis for tone-mapped HDR videos based on EEG and peripheral physiological signals," IEEE Transactions on Autonomous Menta Development, Vol. 7, No. 3, 236-247 (2015)

DISCLOSURE OF INVENTION

Technical Problem

In the above-described Patent literature 1, since a method of determining preference based on a measurement result of a brainwave is not specifically disclosed, there is a problem that a feature amount of the brainwave to be used and a change in a feature amount to be used to determine preference is determined using are not clear.

In addition, Patent literature 2 discloses a configuration of classifying subjective knowledge or interests of subjects using only ERP without conducting a subjective assessment experiment. However, in general, there is a problem that it is not easy to discriminate a tendency common to subjects from the ERP. This is because for assessment terms for subjective knowledge or interests, feature amounts of the ERP or changes in the feature amounts are not clearly determined.

In addition, an individual difference in the feature amount of the ERP is large. Therefore, even when a change in a feature amount can be seen in some of the subjects, the change is not observed at all in the other subjects. That is, there is a problem that it is difficult to execute discrimination with high precision from a change in the ERP in conformity to a certain criterion.

Further, the study described in Non-Patent Literature 1 merely shows that a feature amount of the SSVEP and the subjective assessment result has the correlation, but does not describe execution of a process of classifying assessment target images or a process of determining an image quality.

In addition, the study described in Non-Patent Literature 2 describes a configuration for constructing a model (subject-independent model) independent of a subject by combining VEP and subjective assessment results. However, determination precision of HDR and SDR by this model does not reach 60%. As described in this literature, there is a problem that it is difficult to search for a clear tendency common to subjects by analyzing the VEP.

The present disclosure is devised, for example, in view of the foregoing problems and an object of the present disclosure is to provide an information processing device, an information processing method, and a program capable of executing a process of generating an assessment model for enabling an assessment (subjective assessment) of a user (subject) to a stimulus such as an image to be estimated on the basis of, for example, a brainwave of the user to which the stimulus such as an image presentation process is presented and executing estimation of an assessment value to which the assessment model is applied.

An object of an embodiment of the present disclosure is to provide an information processing device, an information processing method, and a program capable of constructing an assessment model for enabling objective assessment which does not deviate from a subjective assessment result by associating a change in a brainwave appearing as a response of a result obtained by presenting a stimulus to a subject who is an image observer with subjective assessment of the subject in the presented stimulus and capable of assessing a stimulus using the assessment model.

An object of an embodiment of the present disclosure is to provide an information processing device, an information processing method, and a program capable of suppressing a gap between subjects by measuring steady-state visual evoked potential (SSVEP) based on brainwaves of the subjects to improve determination precision of a stimulus such as an assessment target image.

Solution to Problem

A first aspect of the present disclosure is an information processing device including: a brainwave analysis unit configured to measure a brainwave of a subject to which a stimulus is presented and calculate a brainwave feature amount; a subjective assessment analysis unit configured to acquire a subjective assessment value with respect to the stimulus of the subject; and a model construction unit configured to construct an assessment model representing relevance between the brainwave feature amount and the subjective assessment value.

A second aspect of the present disclosure is an information processing device including: a brainwave analysis unit configured to measure a brainwave of a subject to which a stimulus is presented and calculate a brainwave feature amount; a storage unit configured to store an assessment model for enabling a subjective assessment value based on the brainwave feature amount to be acquired; and a stimulus determination unit configured to apply the assessment model to estimate the subjective assessment value from the brainwave feature amount of the subject.

A third aspect of the present disclosure is an information processing method executed in an information processing device including: a brainwave analysis step of measuring a brainwave of a subject to which a stimulus is presented and calculating a brainwave feature amount by a brainwave analysis unit; a subjective assessment analysis step of acquiring a subjective assessment value with respect to the stimulus of the subject by a subjective assessment analysis unit; and a model construction step of constructing an assessment model representing relevance between the brainwave feature amount and the subjective assessment value by a model construction unit.

A fourth aspect of the present disclosure is an information processing method executed in an information processing device including: a brainwave analysis step of measuring a brainwave of a subject to which a stimulus is presented and calculating a brainwave feature amount by a brainwave analysis unit. A stimulus determination unit executes a stimulus determination step of applying an assessment model for enabling a subjective assessment value based on the brainwave feature amount to be acquired to estimate the subjective assessment value from the brainwave feature amount of the subject.

A fifth aspect of the present disclosure is a program causing an information processing device to execute information processing, the program including: a brainwave analysis step of measuring a brainwave of a subject to which a stimulus is presented and calculating a brainwave feature amount in a brainwave analysis unit; a subjective assessment analysis step of acquiring a subjective assessment value with respect to the stimulus of the subject in a subjective assessment analysis unit; and a model construction step of constructing an assessment model representing relevance between the brainwave feature amount and the subjective assessment value in a model construction unit.

A sixth aspect of the present disclosure is a program causing an information processing device to execute information processing, the program including: a brainwave analysis step of measuring a brainwave of a subject to which a stimulus is presented and calculating a brainwave feature amount in a brainwave analysis unit; and a stimulus determination step of applying an assessment model for enabling a subjective assessment value based on the brainwave feature amount to be acquired to estimate the subjective assessment value from the brainwave feature amount of the subject in a stimulus determination unit executes.

Note that a program according to the present disclosure is, for example, a program provided in computer-readable format to an information processing device or a computer system capable of executing various program code, the program being providable by a storage medium or communication medium. By providing such a program in a computer-readable format, processing corresponding to the program is realized on the information processing device or the computer system.

Further objectives, features, and advantages of the present disclosure will be clarified by a more detailed description based on the embodiments of the present disclosure described hereinafter and the attached drawings. Note that in this specification, the term "system" refers to a logical aggregate configuration of multiple devices, and the respective devices of the configuration are not limited to being inside the same housing.

Advantageous Effects of Invention

According to a configuration of an embodiment of the present disclosure, it is possible to realize a configuration capable of constructing an assessment model for enabling a subjective assessment value to be estimated from a brainwave feature amount and acquiring assessment data which does not deviate from a subjective assessment result on the basis of an objective brainwave signal by using the assessment model.

Specifically, an assessment model representing relevance between a brainwave feature amount of a subject and a subjective assessment value of the subject with respect to a stimulus is constructed by presenting the stimulus to the subject. For example, images with different image qualities and a standard image are alternately displayed on a display unit which is a stimulus presentation unit, brainwave feature amount corresponding to an image quality of a subject observing the displayed images and subjective assessment values corresponding to image qualities are acquired, and an image quality assessment model for enabling subjective assessment values to be estimated from the brainwave feature amounts is constructed by machine learning in which the brainwave feature amounts and the subjective assessment values are used as input data.

In this configuration, it is possible to construct an assessment model for enabling subjective assessment values to be estimated from brainwave feature amounts and realize a configuration capable of acquiring assessment data which does not deviate from the subjective assessment result on the basis of objective brainwave signals by using the assessment model.

Note that the advantageous effects described in this specification are merely for the sake of example and non-limiting, and there may be additional advantageous effects.

BRIEF DESCRIPTION OF DRAWINGS

FIG. 14 is an explanatory diagram illustrating a process executed by a result integration unit.

FIG. 22 is an explanatory diagram illustrating a hardware configuration example of an information processing device.

MODE(S) FOR CARRYING OUT THE INVENTION

Figure 1:
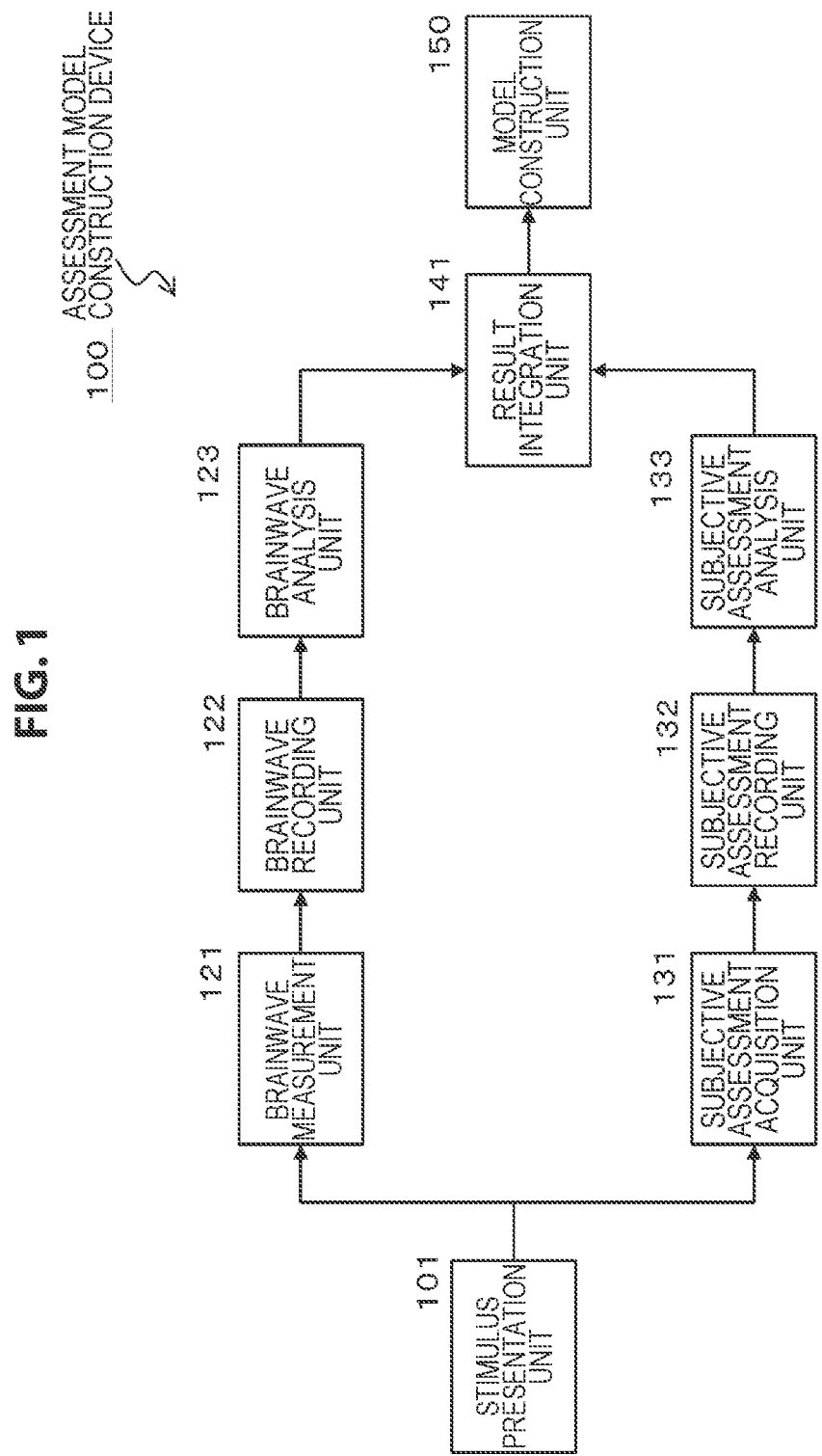
FIG. 1 is an explanatory diagram illustrating a configuration example of an assessment model construction device which is an embodiment of an information processing device according to the present disclosure.

Hereinafter, details of an information processing device, an information processing method, and a program according to the present disclosure will be described with reference to the drawings. Note that the description will be made in accordance with the following sections.

1. Configuration and process of assessment model construction device
2. Details of process executed by stimulus presentation unit
3. Details of processes executed by brainwave measurement unit, brainwave recording unit, and brainwave analysis unit
4. Details of processes of subjective assessment acquisition unit, subjective assessment recording unit, and subjective assessment analysis unit
5. Process executed by result integration unit
6. Details of process executed by model construction unit
7. Process sequence executed by information processing device
8. Configuration and process of assessment model application image quality assessment device
9. Hardware configuration example of information processing device
10. Summary of configuration of present disclosure

[1. Configuration and Process of Assessment Model Construction Device]

A configuration and a process of an information processing device according to the present disclosure will be described with reference to FIG. 1 and the subsequent drawings.

An overall configuration and an overall process of an assessment model construction device 100 which is an embodiment of the information processing device according to the present disclosure will be described with reference to FIG. 1.

Note that an overview of the overall configuration and the overall process of an assessment model construction device 100 will be first described with reference to FIG. 1 and the subsequent drawings. The details of a process of each constituent unit of the assessment model construction device 100 illustrated in FIG. 1 will be described in later sections.

The assessment model construction device 100 illustrated in FIG. 1 constructs, for example, an image quality assessment model for enabling the quality of an image presented to a user (subject) who observes an image to be assessed on the basis of a brainwave measurement result of the user.

The assessment model construction device 100 illustrated in FIG. 1 constructs an assessment model for enabling objective assessment which does not deviate from a subjective assessment value to be executed by associating a change in a brainwave appearing as a response of a result obtained by presenting a stimulus (an image or the like) to a subject who is an image observer with subjective assessment of the subject with respect to the presented stimulus (an image or the like).

By executing image quality assessment based on a brainwave using the assessment model, it is possible to acquire an objective assessment result of an image quality which does not deviate from the subjective assessment.

As described above, for example, as display images displayed on a display unit such as a television, there are images with various image qualities.

Specifically, there are various kinds of images from a high-quality image to a low-quality image, such as a high dynamic range (HDR) image which is a high-quality image with a wide luminance range or outputable color and a standard dynamic range (SDR) image with a narrower luminance range or outputable color than the HDR image.

The images are images subjected to various image quality improvement technologies or compression encoding technologies. For example, even the same HDR images are images of which impressions are different due to differences in processing parameters applied in the various kinds of image processing in some cases.

That is, there are HDR images or HDR images, or the like of which subjective assessment of a user (subject) observing images is high or low.

To calculate image processing parameters for generating HDR images with higher subjective assessment, it is necessary to accumulate subjective assessment results of a user (subject).

However, a process of accumulating subjective assessment results of a user (subject) has a problem that much time and cost are necessary.

One of the methods for solving the problem is to find out correlation between subjective assessment results of a user (subject) and brainwaves of the user (subject).

The assessment model construction device 100 according to the present disclosure constructs an image quality assessment model for enabling an image quality to be assessed on the basis of data indicating correlation between brainwaves obtained at the time of observing, for example, images with different image qualities such as an HDR image and an SDR image and subjective assessment results of a user (subject).

An overview of a processing procedure executed by the assessment model construction device 100 according to the present disclosure is as follows.

Images with various qualities of a high-quality image to a low-quality image such as an HDR image and an SDR image are presented to a user (subject), brainwaves of the subject at the time of presentation of the image with each image quality are measured, and subjective image quality assessment of the subject are acquired.

Further, correlation between the brainwaves (objective assessment) and subjective assessment of the subject when the subject observes the image with each image quality is analyzed on the basis of the acquired data (brainwave measurement results and subjective image quality assessment results), and an image quality assessment model for assessing an image quality on the basis of only a brainwave signal (objective assessment data) is constructed.

The image quality assessment model is an assessment model in which objective assessment of an image quality which does not deviate from a subjective assessment value of an image observer is possible.

By executing image quality assessment based on a brainwave using the assessment model, it is possible to acquire an objective assessment result of an image quality which does not deviate from the subjective assessment.

A configuration and a process of the assessment model construction device 100 according to the present disclosure will be described with reference to FIG. 1 and the subsequent drawings.

As illustrated in FIG. 1, the assessment model construction device 100 includes a stimulus presentation unit 101, a brainwave measurement unit 121, a brainwave recording unit 122, a brainwave analysis unit 123, a subjective assessment acquisition unit 131, a subjective assessment recording unit 132, a subjective assessment analysis unit 133, a result integration unit 141, and a model construction unit 150.

The stimulus presentation unit 101 presents a stimulus to a subject from the outside.

Specifically, a visual stimulus such as an image or a video or an auditory stimulus such as a sound or music is presented. Specification of a stimulus to be presented is assumed to conform to a brainwave measurement scheme.

Note that, as the brainwave measurement scheme, for example, any of the following schemes can be available:

(a) an event-related potential (ERP) measurement scheme;

(b) a visual evoked potential (VEP) measurement scheme; and (c) a steady-state visual evoked potential (SSVEP) measurement scheme.

Note that each of the brainwave measurement schemes is a similar scheme to the schemes disclosed in the above-described Patent Literature 2 and Non-Patent Literatures 1 and 2 and is a brainwave measurement scheme known in the related art.

In a configuration according to the present disclosure, any brainwave measurement scheme may be used.

A specific example of the stimulus presentation unit 101 which is a constituent element of the assessment model construction device 100 according to the present disclosure will be described with reference to FIGS. 2A and 2B.

Figures 2A, 2B:
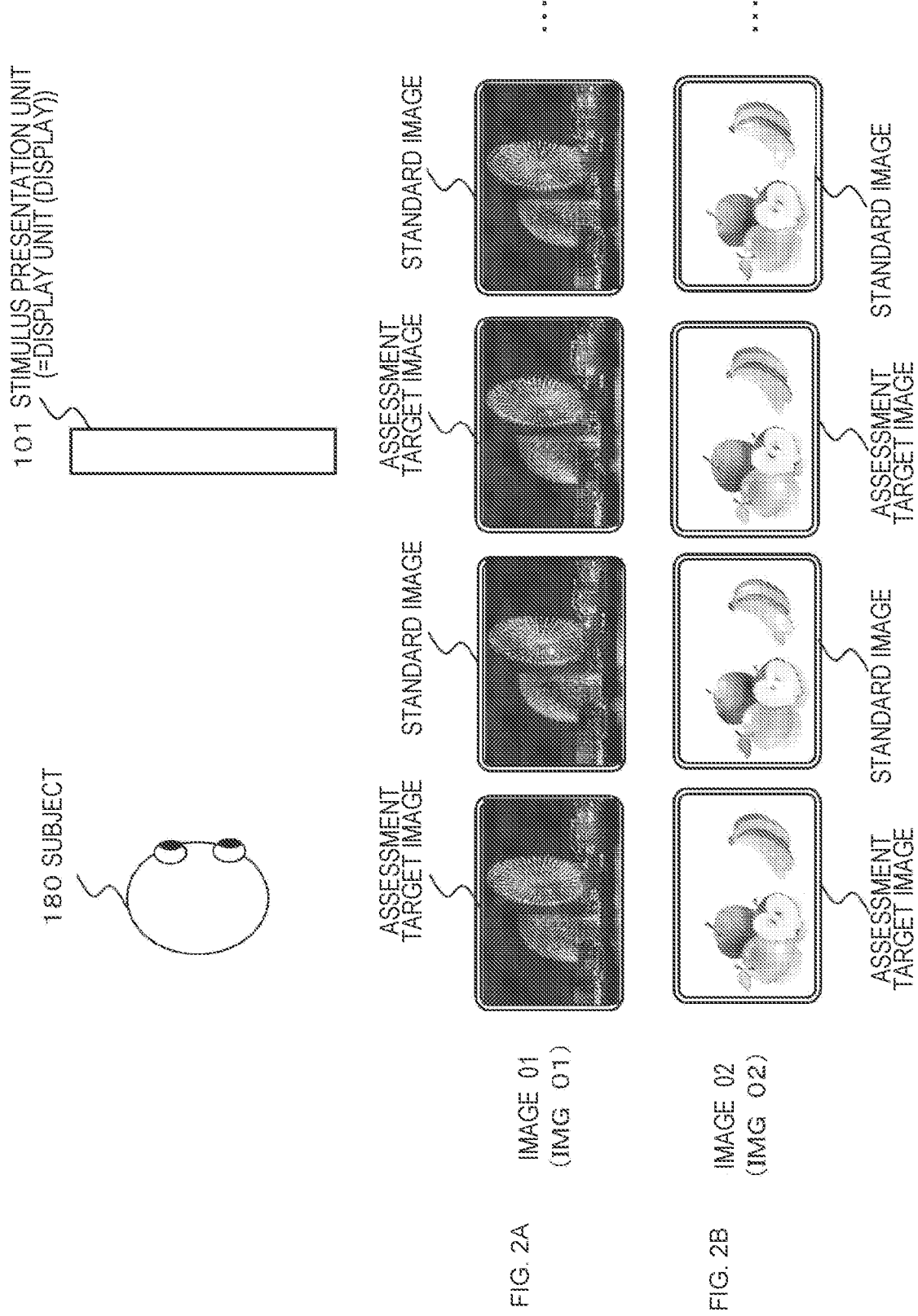
FIGS. 2A and 2B are explanatory diagrams illustrating a specific example of a stimulus presentation unit which is a constituent element of an assessment model construction device 100.

Examples illustrated in FIGS. 2A and 2B are examples in which a display unit (display) that displays an image for a subject 180 is used as the stimulus presentation unit 101.

On the display unit serving as the stimulus presentation unit 101, assessment target image and standard image are alternately displayed at a frequency of, for example, 3 Hz.

That is, for example, setting in which an image presentation frequency is 3 Hz is setting in which display switching of the assessment target image and the standard image is executed three times for 1 second.

Note that the setting of the image presentation frequency=3 Hz is exemplary and another frequency may be applied.

In the case of the image presentation frequency=3 Hz, the subject 180 observes the images alternately displayed at the frequency of 3 Hz.

As the assessment target image, images with various different image qualities, such as an HDR image or an SDR image are used.

The standard image alternately displayed along with the assessment target image is assumed to be an image with the same image quality as all the assessment target images. Specifically, for example, an HDR image can be used as the standard image.

Note that, various different images are used as display objects. For example, various different images with different image qualities from the display objects such as night scene images illustrated in FIG. 2A or fruit images illustrated in FIG. 2B are displayed on the display unit.

When the subject 180 observes the images displayed on the display unit which is the stimulus presentation unit 101, brainwaves based on visual stimuli are output.

The brainwave measurement unit 121 measures a potential change on the scalp of the subject through electrodes (nodes) worn on the head of the subject.

Disposition of the electrodes (nodes) is standard disposition called International 10-20 system, but distinctive disposition or disposition in which the number of electrodes is limited may be used.

In addition, when the electrodes are worn, a gel or an electrolytic solution for improving conductivity is used in some cases or the electrodes are closely adhered by applying pressure mechanically in some cases. Any method may be used.

Note that when brainwaves are recorded, it is necessary to associate the brainwaves with stimuli (images) when the stimuli are presented. Therefore, information regarding timings of the presentation of the stimuli (images) is recorded along with the brainwaves. Further, in a case in which brainwaves of a plurality of subjects are recorded, it is necessary to record the subjects from which brainwave signals are acquired.

Specifically, data such as subjects, presented images, brainwaves, and subjective assessment values of the subjects are associated with each other to be recorded.

Figure 3:
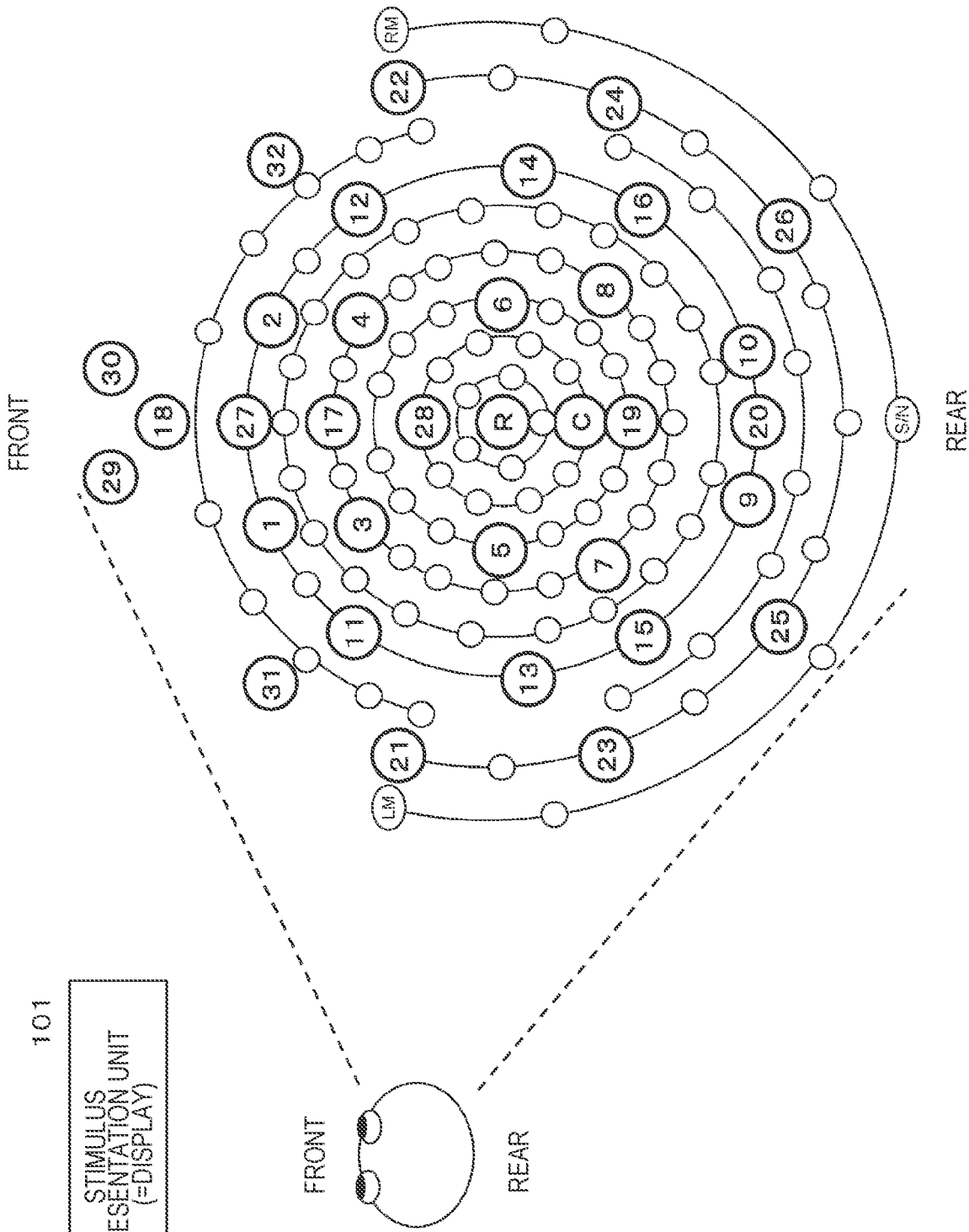
FIG. 3 is an explanatory diagram illustrating a disposition example of electrodes worn on the head of a subject.

An example of disposition of electrodes worn on the head of the subject 180 is illustrated in FIG. 3.

The upper side of FIG. 3 is a head front side of the subject 180 and the lower side of FIG. 3 is a head rear side of the subject 180.

The electrodes are located at 32 positions of 1 to 32 illustrated in FIG. 3.

The brainwave measurement unit 121 measures signals obtained from at least some electrodes among the 32 electrodes illustrated in FIG. 3.

For example, signals obtained from all the 32 electrodes may be used.

Alternatively, only brainwave measurement signals obtained from the electrodes known to measure brainwaves in accordance with visual stimuli, for example, electrode numbers 9, 10, 20, and the like illustrated in FIG. 3 may be configured to be used.

First, as described with reference to FIGS. 2A and 2B, the images, the assessment target image and the standard image, are alternately displayed at a predetermined period, for example, a frequency of 3 Hz, on the display unit serving as the stimulus presentation unit 101.

The subject 180 observes the images alternately displayed at the frequency of 3 Hz.

The brainwave measurement unit 121 measures brainwaves of the subject 180 in accordance with the alternately displayed images.

Note that as measurement signals of the brainwave measurement unit 121, brainwave signals in units of electrodes may be used or an integrated component of a plurality of brainwave signals from the plurality of electrodes (weight-added signal or the like) may be used.

The brainwave recording unit 122 records the brainwaves of the subject acquired from the brainwave measurement unit 121.

Note that since the brainwave is an analog signal, the brainwave is subjected to analog-digital (AD) conversion and is recorded as a digital signal in the brainwave recording unit 122.

In addition, since the brainwave is innately weak, disturbance noise is superimposed in many cases. Therefore, a result signal obtained by removing noise applying a process of a noise removing filter that extracts a brainwave signal with a desired bandwidth by applying a bandpass filter or a notch filter is preferably used as an analysis target.

In this way, the brainwave recording unit 122 preferably generates and records a record signal by executing an arithmetic process of removing a noise component in consideration of a noise component superimposed on a signal when the brainwave recording unit 122 executes a process of recording an analysis result of the brainwaves of the subject acquired by the brainwave measurement unit 121.

The brainwave analysis unit 123 analyzes the brainwaves of the subject 180 recorded in the brainwave recording unit 122.

In the analysis of the brainwaves, it is general to analyze each stimulus in which a change in potential on a time axis or a change in intensity or a phase of the potential on a frequency axis is presented. An item which can be analyzed in accordance with a presented stimulus can be decided in some cases.

Specifically, for example, a stimulus (image) presentation frequency (3 Hz) or an intensity component or a phase component of a secondary harmonic (6 Hz) or a tertiary harmonic (9 Hz) of the frequency in the stimulus presentation unit 101 is acquired.

A specific example of a brainwave analysis process will be described in detail in a later section.

On the other hand, the subjective assessment acquisition unit 131 acquires results of subjective responses by the subject on the basis of a predetermined assessment standard. In general, the responses of the subject 180 are acquired through a manipulation of a keyboard or a mouse or detection of a visual line position in many cases. Any method may be used.

The subjective assessment recording unit 132 records the responses of the subject acquired by the subjective assessment acquisition unit 131.

In consideration of convenience for analysis in a later section, responses input as subjective assessment is recorded in association with stimuli (images) to which the responses are given.

As described above, data such as subjects, presented images, brainwaves, and subjective assessment values of the subjects are associated with each other to be recorded.

The subjective assessment analysis unit 133 analyzes the responses of the subject recorded by the subjective assessment acquisition unit 132.

The result integration unit 141 integrates the brainwaves analyzed by the brainwave analysis unit 123 with the subjective assessment analyzed by the subjective assessment analysis unit 133 in association therewith.

Specifically, learning data to be used in the model construction unit 150 in a later section is generated by associating the brainwaves at the time of presentation of the stimuli to the subject 180 with the subjective assessment.

The model construction unit 150 executes machine learning using information obtained in the result integration unit 141 as learning data to construct an assessment model representing relevance between a brainwave feature amount and subjective assessment. Specifically, the model construction unit 150 constructs an image quality assessment model for enabling an image quality which is a subjective image quality result of an image presented to a user (subject) observing the image to be determined on the basis of a brainwave measurement result of the user.

Learning data which is applied to machine learning in the model construction unit 150 includes student data and supervisor data, and supervised machine learning is executed. Here, the student data is data related to a feature amount of a brainwave and the supervisor data is data related to subjective assessment.

The model construction unit 150 executes a machine learning process using the learning data to construct an image quality assessment model for enabling a subjective assessment image quality of an image presented to the user to be determined on the basis of a brainwave measurement result of a user (subject) observing the image.

The overview of the overall configuration and the overall process of the assessment model construction device 100 according to the present disclosure illustrated in FIG. 1 has been described above.

Hereinafter, specific processes of the constituent units of the assessment model construction device 100 according to the present disclosure illustrated in FIG. 1 will be described in sequence.

[2. Details of Process Executed by Stimulus Presentation Unit]

First, the details of a process executed by the stimulus presentation unit 101 of the assessment model construction device 100 illustrated in FIG. 1 will be described.

The stimulus presentation unit 101 of the assessment model construction device 100 illustrated in FIG. 1 alternately displays images, an assessment target image and a standard image, at a predetermined period, for example, a frequency of 3 Hz, as described above with reference to FIGS. 2A and 2B.

The subject 180 observes the images alternately displayed at the frequency of 3 Hz.

When the subject 180 observes the images displayed on the display unit which is the stimulus presentation unit 101, brainwaves based on visual stimuli are output.

The images presented to the subject 180 are images with various different image qualities, such as an HDR image and an SDR image.

Examples of specific presented images will be described with reference to FIG. 4.

Figure 4:
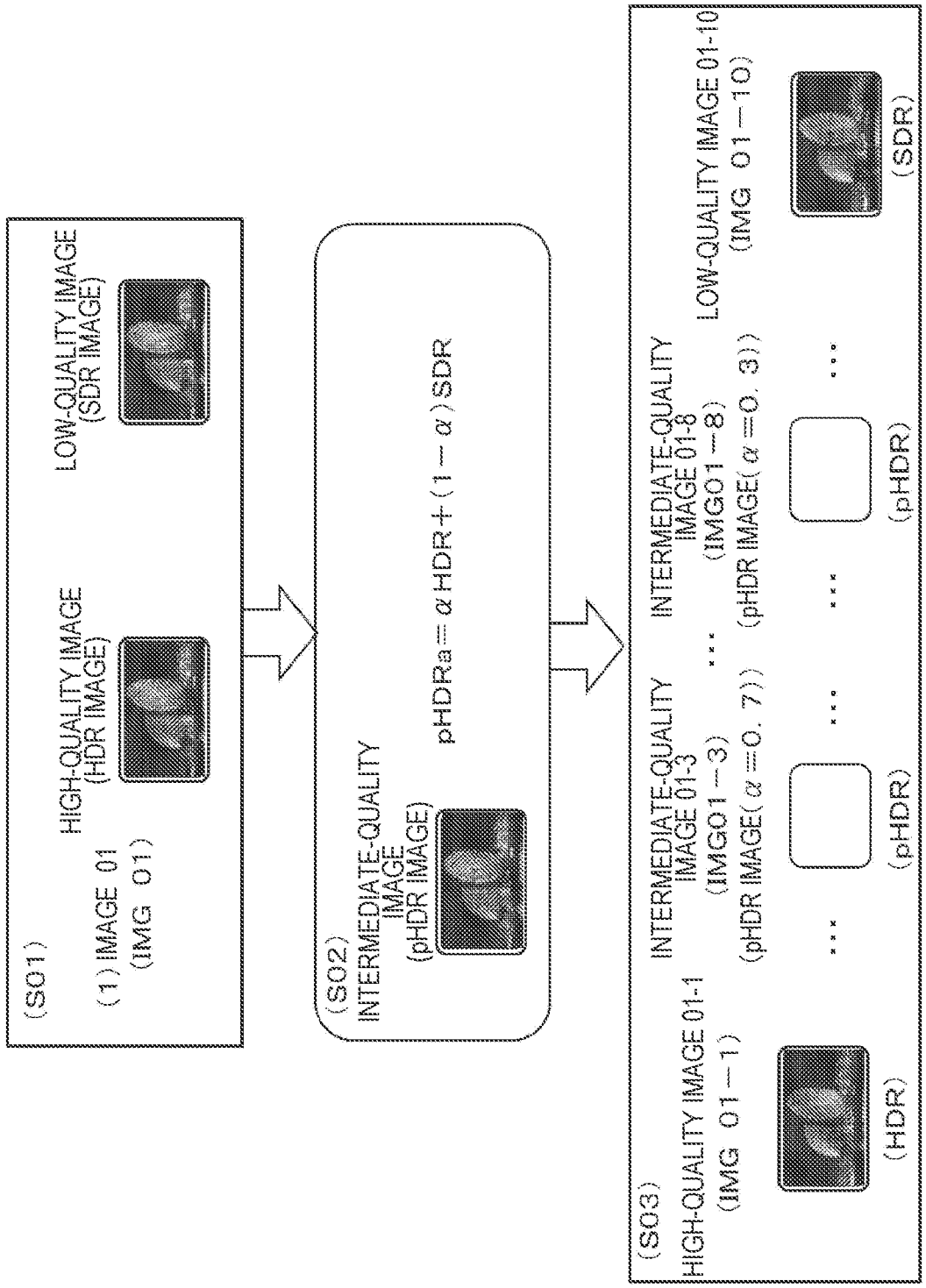
FIG. 4 is an explanatory diagram illustrating a specific example of an image presented to the subject.

First, as illustrated in (step S01) of FIG. 4, a high-quality image, for example, an HDR image, and a low-quality image, for example, an SDR image, which are images of the same object are prepared.

Subsequently, as illustrated in (step S02), a plurality of intermediate-quality images (pHDR images) is generated on the basis of two kinds of images (HDR/SDR).

In the process of generating the intermediate images, for example, a α blend process for each corresponding pixel value can be generated.

The pixel values pHDRa of the intermediate-quality images (pHDR images) are decided in a calculation expression in which the following α blend process is executed:

$$pHDRa = \alpha HDR + (1-\alpha) SDR.$$

Note that HDR and SDR in the foregoing expression are the same pixel values of the HDR image and the SDR image.

A value of α in the foregoing expression is set in the range of 0 to 1.0.

The image quality is higher as the value of α is larger (closer to 1). The image quality is lower as the value of α is less (closer to 0).

The value of α is set to various values and the intermediate-quality images with a plurality of different image qualities are generated.

For example, an example illustrated in (step S03) of FIG. 4 is an example in which images with ten kinds of different image qualities are generated including an HDR image and an SDR image.

That is, the example is an example in which the value of α is set to eight kinds of different values and eight kinds of intermediate-quality images with different image qualities are generated.

As a result, the following images with ten kinds of different image qualities are set:

(1) a high-quality image 01-1 (IMG 01-1) (=HDR image);

(2) to (9) intermediate-quality images 01-2 to 9 (IMG 01-2 to 9) (=pHDR images (α blend images)); and

(10) a low-quality image 01-10 (IMG 01-10) (=SDR image).

The image presentation unit 101 sequentially displays the ten kinds of assessment target images.

An image output example in a display method will be described with reference to FIG. 5.

Figure 5:
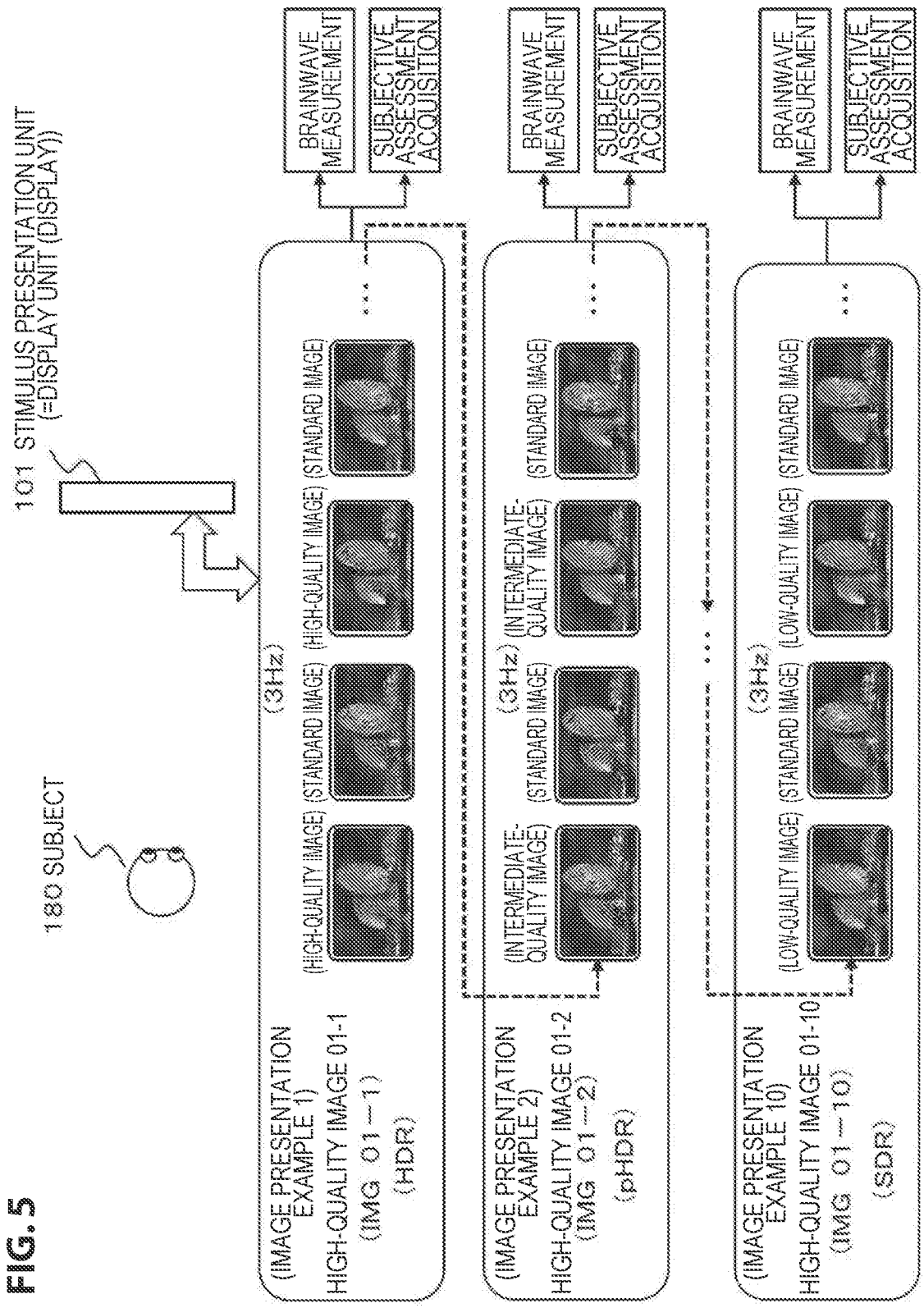
FIG. 5 is an explanatory diagram illustrating an example of a process of generating a blend image using an HDR image and an SDR image as a process of generating an output image in an image presentation unit.

(Image presentation example 1) illustrated in FIG. 5 is an example in which the high-quality image 01-1 (IMG 01-1) (=HDR image) is displayed on the display unit which is the stimulus presentation unit 101.

The images, the assessment target image and the standard image, are alternately displayed at a predetermined period, for example, a frequency of 3 Hz.

That is, the image presentation frequency is 3 Hz and the assessment target image and the standard image are alternately displayed three times for 1 second.

Note that the setting of the image presentation frequency=3 Hz is exemplary and another frequency may be applied.

For example, the high-quality image (HDR image) is used as the standard image.

In the case of the image presentation frequency=3 Hz, the subject 180 observes the images, the alternately displayed assessment target image and standard image, at the frequency of 3 Hz.

When the subject 180 observes the images displayed on the display unit which is the stimulus presentation unit 101, brainwaves based on visual stimuli are output.

The brainwave measurement unit 121 measures the brainwaves.

Further, the subject 180 observes the alternately displayed images, executes image quality assessment of the observed images, and records or inputs the assessment values. The subjective assessment values are input to the subjective assessment acquisition unit 131.

(Image presentation example 2) illustrated in FIG. 5 is executed after (image presentation example 1) illustrated in FIG. 5.

(Image presentation example 2) illustrated in FIG. 5 is an example in which the intermediate-quality image 01-2 (IMG 01-2) (=pHDR image) is displayed on the display unit which is the stimulus presentation unit 101.

In (image presentation example 2), the assessment target image and the standard image are also alternately displayed three times for 1 second.

Note that the standard image used herein is assumed to be the same image as the standard image used in (image presentation example 1).

In (image presentation example 2), the brainwave measurement and a subjective assessment acquisition process are also executed similarly.

(Image presentation example 10) illustrated in FIG. 5 is an example in which the low-quality image 01-10 (IMG 01-10) (=SDR image) is displayed on the display unit which is the stimulus presentation unit 101.

In (image presentation example 10), the assessment target image and the standard image are also alternately displayed three times for 1 second.

Note that the standard image used herein is assumed to be the same image as the standard image used in (image presentation example 1).

In (image presentation example 10), the brainwave measurement and a subjective assessment acquisition process are also executed similarly.

In this way, a process of alternately displaying the assessment target image and the standard image with a given image quality on the display unit which is the stimulus presentation unit 101 and changing the assessment target image in units of predetermined periods (for example, images with ten kinds of image qualities) is executed. In each display process, brainwave measurement and subjective assessment value acquisition processes are executed.

Note that in the above-described examples, the example in which the high-quality image (HDR image) is used as the standard image has been described. As the standard image, it is sufficient if an image with a given image quality is used, and an image other than the high-quality image (HDR image) may be used.

Note that, further, a similar process is executed on various images that have different display objects.

Figure 6:
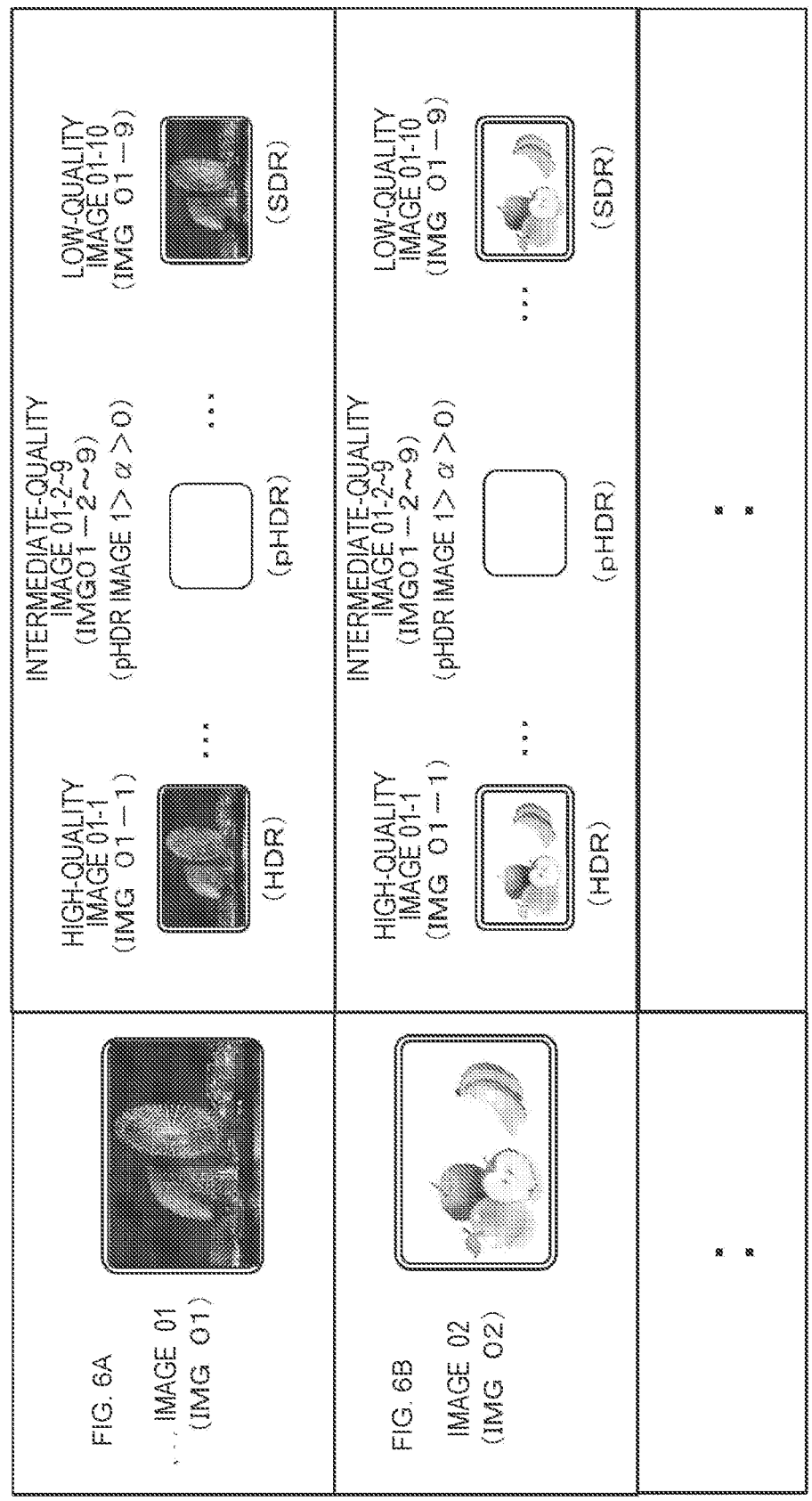
FIGS. 6A and 6B are explanatory diagrams illustrating an image output example in the image presentation unit.

As illustrated in FIGS. 6A and 6B, with regard to the image 01 (IMG-01), images with a plurality of kinds (for example, ten kinds) of different image qualities are presented to the subject and the brainwave measurement and subjective assessment value acquisition processes from the subject are executed.

Further, with regard to the image 02 (IMG-02) that has a different display object from the image 01 (IMG-01), images with a plurality of kinds (for example, ten kinds) of different image qualities are presented to the subject and the brainwave measurement and subjective assessment value acquisition processes from the subject are executed.

More kinds of images may be used. For example, it is preferable to execute a process of applying about three to ten kinds of images with different features, presenting the images with different image qualities to the subject, and executing the brainwave measurement and the subjective assessment value acquisition process from the subject.

Note that in the process described above with reference to FIG. 4, that is, the process of generating the intermediate-quality images with different image qualities, the α blend process using the HDR image and the SDR image has been set to be executed. However, the HDR image and the SDR image on which luminance adjustment is executed may be configured to be used as original images on which the α blend process is executed.

The example will be described with reference to FIG. 7.

Since the HDR image and the SDR image have different output luminance ranges, the SDR image gives a darker impression than the HDR image.

Due to brightness and darkness of the images, the subject may make subjective assessment showing that the quality of the SDR image is poor in some cases.

To solve the difference between the brightness and darkness of the images, a luminance-adjusted SDR image obtained by increasing the luminance of the entire SDR image is generated and an intermediate-quality image is generated through the α blend process based on the HDR image and the luminance-adjusted SDR image.

Figure 7:
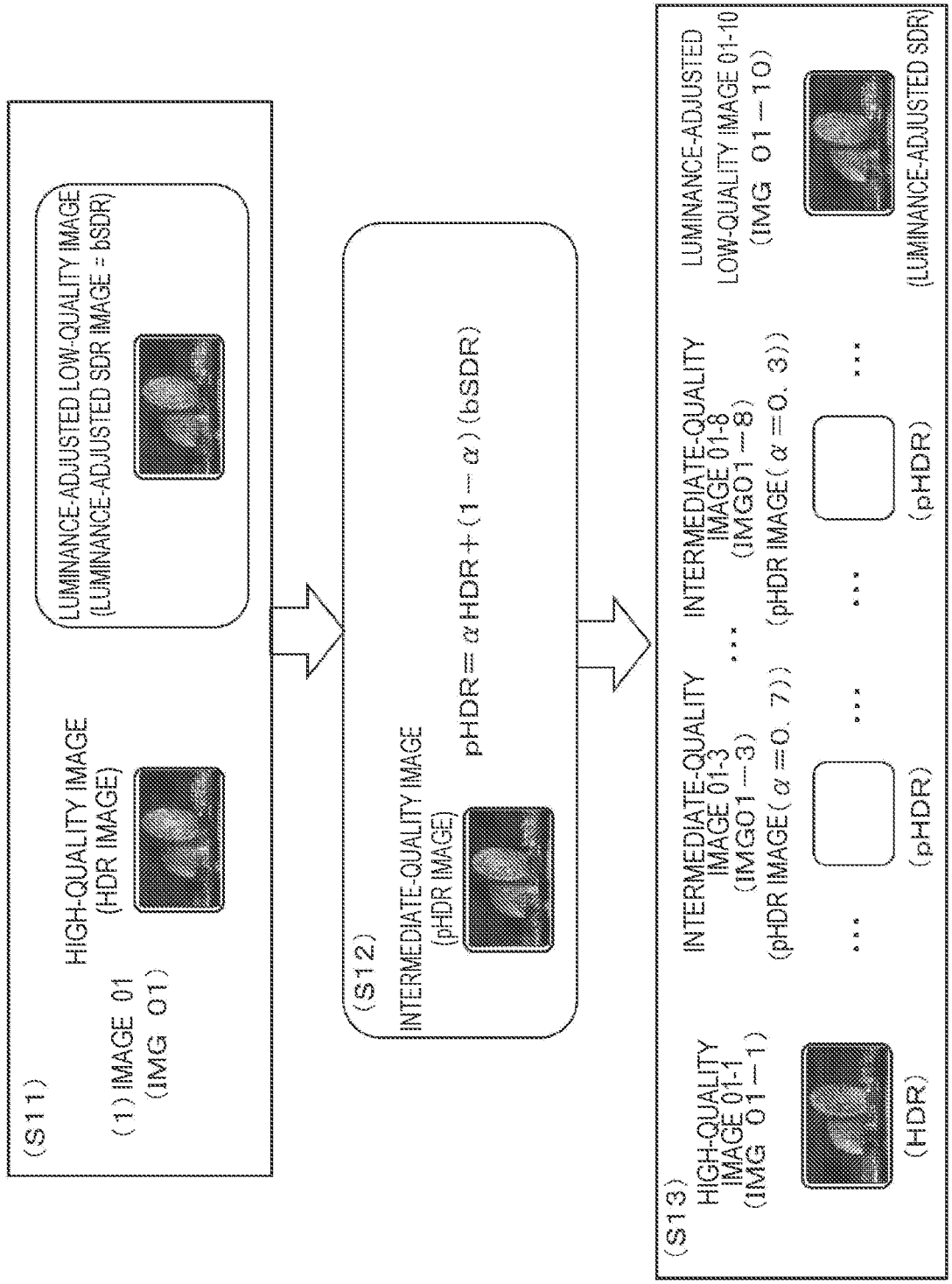
FIG. 7 is an explanatory diagram illustrating a process of generating a blend image using an HDR image and an SDR image with adjusted luminance.

The example illustrated in FIG. 7 is an example in which images with ten kinds of different image qualities are generated including the HDR image and the luminance-adjusted SDR image.

The following images with ten kinds of different image qualities are set:

(1) a high-quality image 01-1 (IMG 01-1) (=HDR image);

(2) to (9) intermediate-quality images 01-2 to 9 (IMG 01-2 to 9) (=pHDR images (α blend images)); and

(10) a luminance-adjusted low-quality image 01-10 (IMG 01-10) (=luminance-adjusted SDR image).

In this way, the images with the plurality of kinds of different image qualities set so that the luminance felt from the entire images is substantially matched may be configured to be generated and presented to the subject.

[3. Details of Processes Executed by Brainwave Measurement Unit, Brainwave Recording Unit, and Brainwave Analysis Unit]

Next, the details of processes executed by the brainwave measurement unit 121, the brainwave recording unit 122, and the brainwave analysis unit 123 of the assessment model construction device 100 illustrated in FIG. 1 will be described.

As described above, the brainwave measurement unit 121 executes brainwave measurement in accordance with, for example, any of the following schemes in accordance with specification of a stimulus present by the stimulus presentation unit 101.

(a) an event-related potential (ERP) measurement scheme;

(b) a visual evoked potential (VEP) measurement scheme; and (c) a steady-state visual evoked potential (SSVEP) measurement scheme.

Note that analysis target data of a brainwave to a presentation stimulus differs in accordance with a measurement scheme to be applied.

For example, in a case in which a time or frequency change in a brainwave to a presentation stimulus is analyzed, it is preferable to assess ERP or VEP.

In the measurement of the ERP or the VEP, how potential after stimulus presentation changes temporally, such as a negative potential change (N2) about after 200 milliseconds in the stimulus presentation or a positive potential change (P300) about after 300 milliseconds in the stimulus presentation is noticed, or how power of a frequency component such as a δ wave, a θ wave, a α wave, a β wave, or a γ wave included in a brainwave changes temporally is noticed.

When the ERP or the VEP is measured, multilateral analysis on a spatial axis (electrode), a time axis, and a frequency axis is possible. In contrast, there is the disadvantage that it is difficult to determine whether there is a meaningful difference in an obtained result.

On the other hand, in a case in which a frequency change to a presentation stimulus is specialized and analyzed, it is preferable to assess the SSVEP. In the measurement of the SSVEP, a standard stimulus and an assessment target stimulus are caused to be alternately displayed at a predetermined presentation frequency.

For example, the example described above with reference to FIG. 5 is equivalent to an alternate display example of the images in the process of measuring the SSVEP. An assessment target stimulus is an assessment target image and a standard stimulus is a standard image. A presentation frequency is 3 Hz.

In this way, by causing the assessment target stimulus to be changed at each predetermined time, the subject gradually perceives a difference between the standard stimulus and the assessment target stimulus, and the difference appears as a brainwave.

In the case of the SSVEP, potential is converted into a frequency component, and the presentation frequency and a change in the intensity or the phase of a secondary or tertiary harmonic are analyzed. When each assessment target stimulus is presented, how the intensity or the phase changes is noticed. When the SSVEP is assessed, there is the advantage that whether a brainwave changes with regard to the assessment target stimulus, for example, whether the intensity of the frequency component changes, can clearly be apprehended.

Hereinafter, a process example of a case in which a process of analyzing a frequency component of a brainwave applying the SSVEP as a brainwave measurement scheme and extracting intensity at a regular frequency is executed will be described.

The regular frequency is assumed to be a presentation frequency or the secondary or tertiary harmonic of a stimulus, as described above.

In the image presentation example described above with reference to FIG. 5, the presentation frequency is 3 Hz. That is, an image and a standard image are set to be alternately displayed three times for 1 second.

In this case, the frequency component of an analysis target brainwave is a frequency component such as 3 Hz, or 6 Hz, 9 Hz, or the like which is the secondary or tertiary harmonic.

To obtain a clear response at the frequency, the time frequency is preferably set to about several Hz, but a response at another time frequency can also be obtained.

Figure 8:
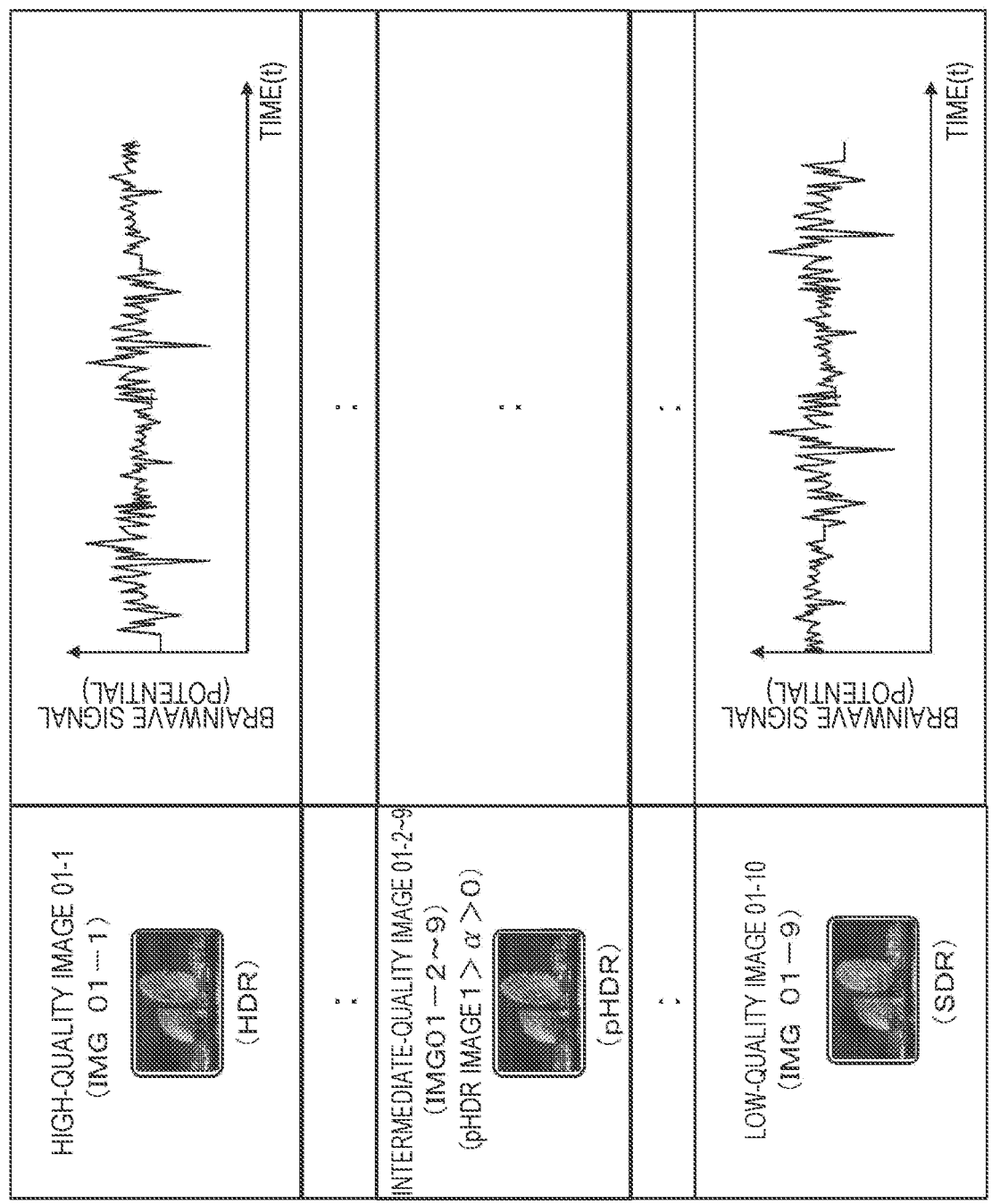
FIGS. 8A and 8B are explanatory diagrams illustrating an example of a brainwave signal detected from the electrodes.

In the electrode setting example described above with reference to FIG. 3, an example of a brainwave signal detected from one certain electrode, for example, an electrode 9, is illustrated in FIGS. 8A and 8B.

FIG. 8A illustrates an example of a brainwave signal (potential) obtained when the high-quality image 01-1 (IMG 01-1) (=HDR image) and the standard image are alternately displayed at 3 Hz. The horizontal axis represents the time and the vertical axis represents the brainwave signal (potential).

Note that a brainwave signal example illustrated in FIGS. 8A and 8B are diagrams for describing a concept of the brainwave signal and is not data of actual measurement signal itself.

FIG. 8B illustrates an example of a brainwave signal obtained when the low-quality image 01-10 (IMG 01-10) (=SDR image) and the standard image are alternately displayed at 3 Hz.

The brainwave signal measured in accordance with the quality of an image to be presented differs.

Figure 9:
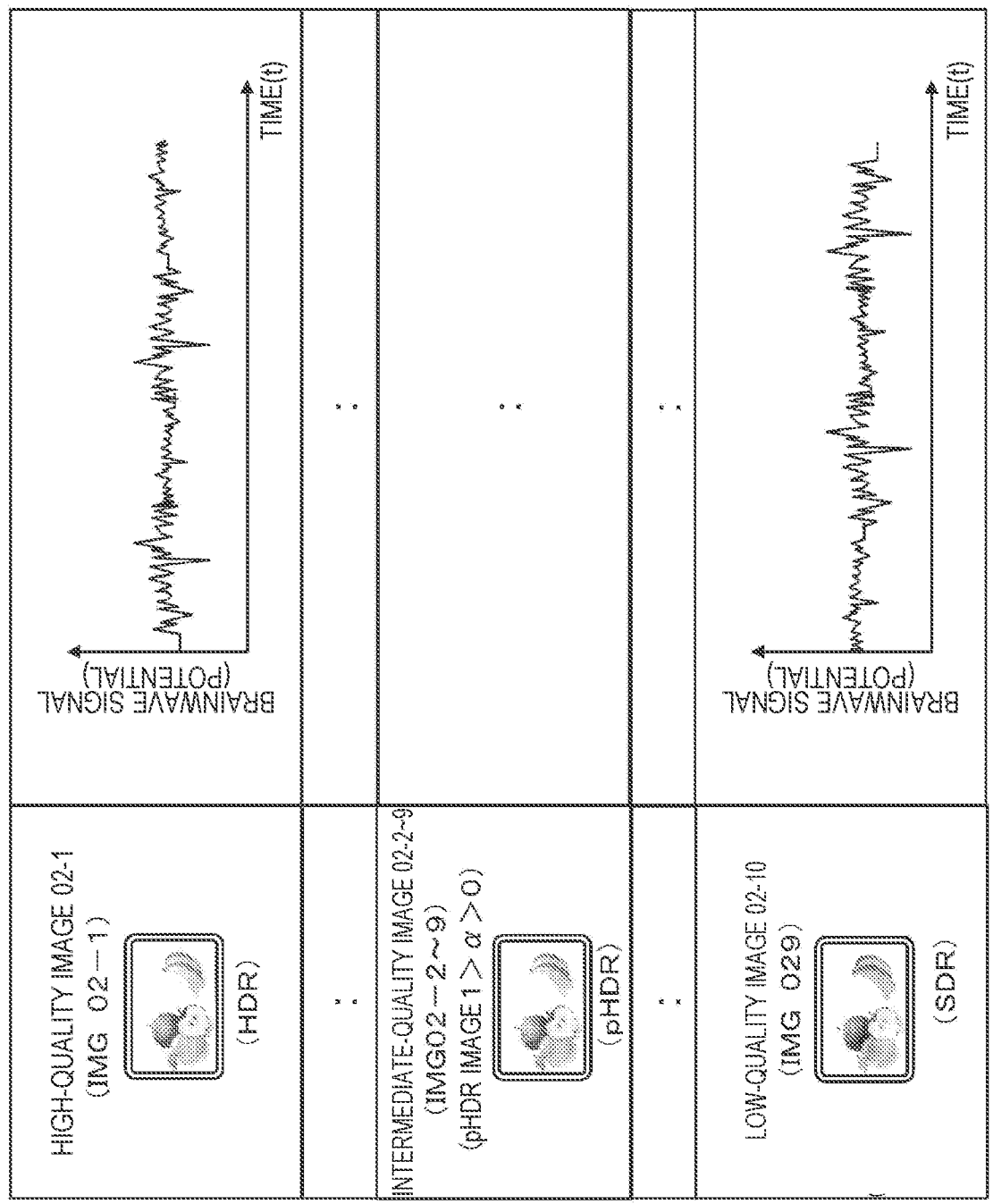
FIGS. 9A and 9B are explanatory diagrams illustrating an example of a brainwave signal detected from the electrodes.

In a case in which a fruit image 02 different from a night scene image 01 illustrated in FIGS. 8A and 8B is presented, an example of a brainwave signal detected from one certain electrode, for example, the electrode 9, is illustrated in FIGS. 9A and 9B.

FIG. 9A illustrates an example of a brainwave signal (potential) obtained when the high-quality fruit image 02-1 (IMG 02-1) (=HDR image) and the standard image are alternately displayed at 3 Hz. The horizontal axis represents the time and the vertical axis represents the brainwave signal (potential).

FIG. 9B illustrates an example of a brainwave signal obtained when the low-quality image 02-10 (IMG 02-10) (=SDR image) and the standard image are alternately displayed at 3 Hz.

In this way, the brainwave signal measured in accordance with an object included in the image differs as well as the quality of the image to be presented.

Note that the brainwave measurement unit 121 measures, for example, a potential change for each electrode described with reference to FIG. 3.

The examples of the brainwave signals illustrated in FIGS. 8A 8B, 9A and 9B have been described as the example of the signal (potential) detected from one electrode of the plurality of electrodes illustrated in FIG. 3. However, an added signal of potential of the plurality of electrodes or a weight-added signal in which a weight regulated in advance at each electrode position is used may be configured to be acquired.

Note that in a case in which the number of detection target electrodes is N, a measurement result of a brainwave is expressed as a combination of N-dimensional spatial vector data and 1-dimensional time data. In a case in which N is large, an amount of data is vast. Therefore, an axis efficiently expressing a feature amount of the spatial vector data may be found out using independent component analysis or the like, a projection matrix may be obtained, and a configuration using the result may be used. This scheme is synonymous with a scheme of projecting N-dimensional spatial vector data to another space and causing the dimension to be less than N.

Note that the magnitude of a change in the potential of the brainwave itself differs for each subject since any of the ERP, the VEP, and the SSVEP is a signal weak in units of μV.

Therefore, even when the SSVEP is measured for a plurality of subjects under the same condition, there is a possibility of the intensity of the signal considerably varying. In this way, in a case in which an average or dispersion of a data group acquired under the same condition considerably differs for each subject, it is preferable to execute a conversion process of setting the average to 0 and setting the dispersion to 1 and execute analysis using the conversion result.

Note that the data conversion process is referred to as data standardization. By standardizing the data, the variation between the subjects is absorbed and the data can be analyzed in the same criterion.

As described above, in the case of the SSVEP, potential is converted into a frequency component, and the presentation frequency and a change in the intensity of a secondary or tertiary harmonic are analyzed. When each assessment target stimulus is presented, how the intensity changes is noticed. When the SSVEP is assessed, there is the advantage that whether a brainwave changes with regard to the assessment target stimulus, i.e., whether the intensity of the frequency component changes, can clearly be apprehended.

In a case in which the SSVEP is applied as a brainwave measurement scheme, a frequency component of the SSVEP is analyzed and the magnitude of the signal at a regulated frequency can be defined as intensity.

For example, when frequency component analysis of a specific frequency (3 Hz, 6 Hz, 9 Hz, or the like) is executed on the brainwave signal (potential) which is measurement data detected from the electrodes illustrated in FIGS. 8A and 8B or 9A and 9B, a peak is detected at a period equivalent to the specific frequency (3 Hz, 6 Hz, 9 Hz, or the like) in some cases.

For example, by executing Fourier transform on the brainwave signal (potential) which is the measurement data, it is possible to obtain a peak signal with a peak at a specific frequency (3 Hz, 6 Hz, 9 Hz, or the like) in some cases. The peak signal with the specific frequency is a signal in accordance with a period of the presented images and can be analyzed as a brainwave occurring on the basis of the presented images. By defining the magnitude of the signal with the specific frequency as intensity of the brainwave signal and acquiring the intensity in units of presented images for analysis, it is possible to acquire a brainwave intensity signal in accordance with an image or an image quality.

Here, a measurement signal includes noise caused in an external environment, noise specific to a device, biometric signal noise of a subject, or the like. A final brainwave intensity signal Fi is preferably calculated by removing a noise component Ni from a detection intensity signal Si obtained from the measurement signal.

Figure 10:
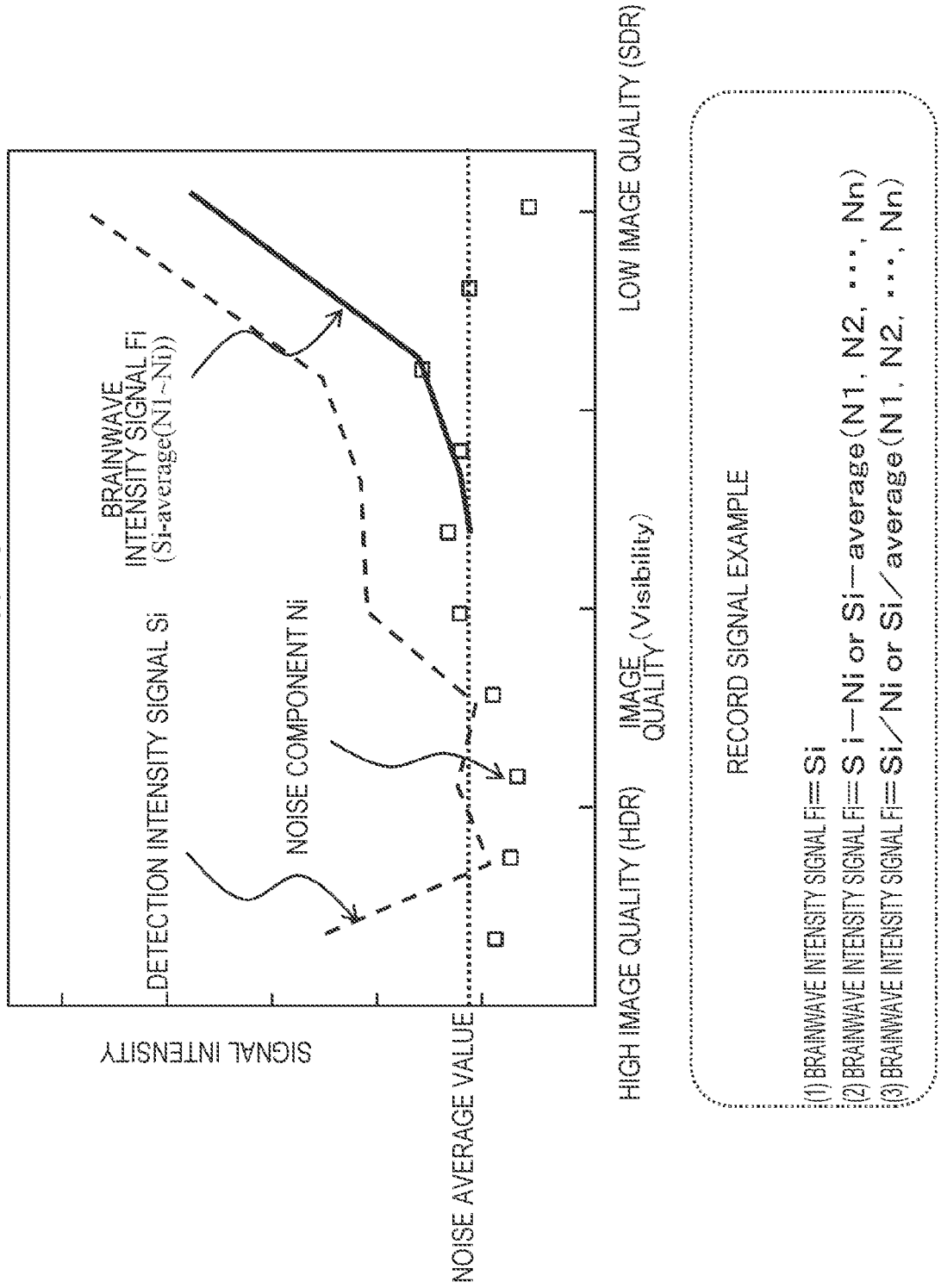
FIG. 10 is a diagram illustrating examples of a detection intensity signal Si, a noise component Ni, and a brainwave intensity signal Fi calculated from brainwave signals (potentials) which are measurement data detected from the electrodes.

FIG. 10 illustrates examples of the detection intensity signal Si and the noise component Ni calculated from the brainwave signal (potential) which is the measurement data detected from the electrodes illustrated in FIGS. 8A and 8B or 9A and 9B, and the brainwave intensity signal Fi calculated by removing the noise component Ni from the detection intensity signal Si.

In the graph illustrated in FIG. 10, the horizontal axis represents image quality (visibility level) displayed on the display unit which is the stimulus presentation unit 101.

The left side is set to indicate better image quality and the right side is set to indicate poorer image quality.

The vertical axis represents signal intensity.

The detection intensity signal Si shown in the graph of FIG. 10 is, for example, a signal obtained on the basis of ten kinds of brainwave signal (potential) data obtained by sequentially presenting images with ten kinds of different image qualities of the image 01 illustrated in FIGS. 8A and 8B.

As described above, frequency component analysis of the specific frequency (3 Hz) is executed on the brainwave signal (potential) which is measurement data detected from the electrode, a peak value of the period equivalent to the specific frequency (3 Hz) is detected as brainwave intensity, and a line connecting the signal intensity in units of images with the image qualities is the detection intensity signal Si shown in the graph of FIG. 10.

Here, the detection intensity signal Si includes noise caused due to various external environments, noise specific to a device, biometric signal noise of a subject, or the like. The signal intensity of the noise is the noise component Ni illustrated in FIG. 10.

Note that i is an identification parameter indicating the number of measurements. In the example illustrated in the drawing, i is a measurement processing result obtained by presenting images with ten kinds of different image qualities and i=1 to 10.

The brainwave analysis unit 123 calculates the final brainwave intensity signal Fi by removing the noise component Ni from the detection intensity signal Si and outputs the final brainwave intensity signal Fi to the result integration unit 141. In addition, alternatively, the brainwave intensity signal Fi is stored in a storage unit.

Specifically, for example, the brainwave analysis unit 123 calculates the final brainwave intensity signal Fi by applying any of the following calculation expressions and outputs the final brainwave intensity signal Fi to the result integration unit 141 or the storage unit:

(example 1) brainwave intensity signal Fi=Si;
(example 2) brainwave intensity signal Fi=Si−Ni;
(example 3) brainwave intensity signal Fi=Si−average (where N1, N2, . . . , Nn);
(example 4) brainwave intensity signal Fi=Si/Ni; and
(example 5) brainwave intensity signal Fi=Si/average (where N, N2, . . . Nn).

The (example 1) brainwave intensity signal Fi=Si is an example in which the detection intensity signal Si is used, as it is, as the brainwave intensity signal Fi without subtracting the noise component.

The (example 2) brainwave intensity signal Fi=Si−Ni is an example in which the noise component (Ni) is subtracted from the detection intensity signal Si in units of each measurement (i) to calculate the brainwave intensity signal Fi.

The (example 3) brainwave intensity signal Fi=Si−average (where N1, N2, . . . , Nn) is an example in which an average value of the noise component (Ni) is calculated and the brainwave intensity signal Fi is calculated by subtracting a noise component average value from the detection intensity signal Si.

The (example 4) brainwave intensity signal Fi=Si/Ni is an example in which a ratio of the detection intensity signal Si to the noise component (Ni) is set as the brainwave intensity signal Fi by dividing the detection intensity signal Si by the noise component (Ni) in units of each measurement (i).

The (example 5) brainwave intensity signal Fi=Si/average (where N, N2, . . . , Nn) is an example in which an average value of the noise component (Ni) is calculated and a ratio of the detection intensity signal Si to the average value of the noise component (Ni) is set as the brainwave intensity signal Fi by dividing the detection intensity signals Si by the average value of the noise components (Ni).

In this way, the brainwave analysis unit 123 executes a calculation process of removing the noise component in consideration of the noise component superimposed on the detection intensity signal Si of the subject acquired by the brainwave measurement unit 121 to generate the brainwave intensity signal Fi and outputs the brainwave intensity signal Fi to the result integration unit 141. In addition, alternatively, the brainwave intensity signal Fi is stored in the storage unit.

Figure 11:
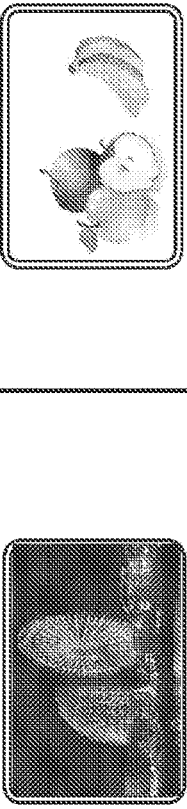
FIG. 11 is a diagram illustrating an example of data acquired by a brainwave analysis unit on the basis of data obtained by setting images with a plurality (10 kinds) of different image qualities as assessment target images in images 01, 02, and the like configured from different display objects and alternately displaying the assessment target images and a standard image at a specific frequency (3 Hz).

FIG. 11 is a diagram illustrating an example of data acquired by the brainwave analysis unit 123 on the basis of data obtained by alternately displaying images with a plurality (10 kinds) of different image qualities along with the standard image in each of the images 01, 02, and the like configured from different display objects at the specific frequency (3 Hz).

The noise Ni and the detection intensity signal Si generated by detecting a peak value of the period of two kinds of different frequencies (3 Hz and 6 Hz) as intensity at the measurement potential of the electrodes worn on the subject 180 are illustrated.

The brainwave analysis unit 123 executes any of a process of acquiring the detection intensity signal Si of the subject obtained through the process of presenting the plurality of images and images with different image qualities and a process of generating the brainwave intensity signal Fi by executing a calculation process of removing the noise component and outputting the brainwave intensity signal Fi to the result integration unit 141 or storing the brainwave intensity signal Fi in the storage unit.

Note that the brainwave intensity signal Fi is output to the result integration unit 141 or is stored in the storage unit in association with the subject and the image.

[4. Details of Processes of Subjective Assessment Acquisition Unit, Subjective Assessment Recording Unit, and Subjective Assessment Analysis Unit]

Next, the details of processes executed by the subjective assessment acquisition unit 131, the subjective assessment recording unit 132, and the subjective assessment analysis unit 133 of the assessment model construction device 100 illustrated in FIG. 1 will be described.

For example, as a subjective assessment processing scheme for the images, for example, there is the following assessment scheme.

n-stage assessment (MOS: Mean Opinion Score), (where n=5, 7, or the like);
score assessment (magnitude estimation method or the like); and
introspective assessment (comment recording)

In a case in which assessment is executed using the MOS, 5-stage assessment or 7-stage assessment is used in many cases. In the case of the 5-stage assessment, an assessment value in the range of 1 point to 5 points is set in each assessment target image. In the 7-stage assessment, a score is set in the range of 1 point to 7 points.

The meaning of each point is regulated in advance and is announced beforehand as an assessment standard to the subject. Normally, there are the following assessment standards:

absolute assessment (absolute category rating: ACR); and
degradation assessment (degradation category rating: DCR).

Note that in the case of assessment by the MOS, a numerical value of the recorded MOS can be used, as it is, to be seen as a subjective assessment result.

As another subjective assessment scheme, a scheme of comparing a set threshold with a numerical value of the MOS, determining which is larger, and setting two classification assessment results in which 1 is set when the numerical value is greater than the threshold and 0 is set when the numerical value is less than the threshold can also be applied, in each image.

As still another subjective assessment scheme, whether or not there is a statistical significance between a numerical value which is a standard and a numerical value of the MOS which is a comparison target may be determined by a statistical test.

Specifically, this scheme is a scheme of using a t-test to determine whether there is a statistical significance between an average value of numerical values of the MOS to a standard stimulus regulated separately and an average value of numerical values of the MOS to stimuli of assessment targets in which a feature amount of the standard stimulus is changed.

A process example executed by the subjective assessment acquisition unit 121 will be described with reference to FIG. 12.

Figure 12:
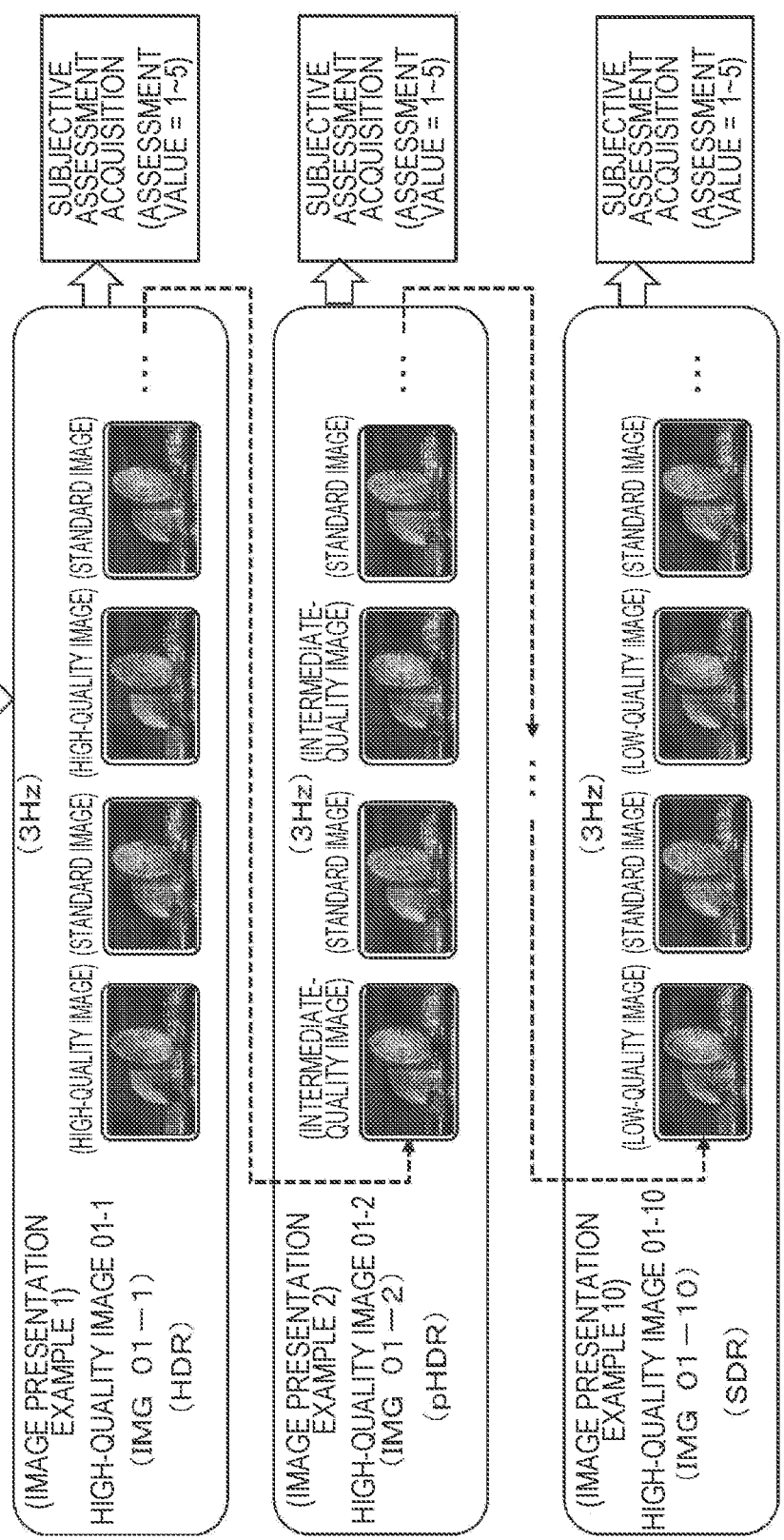
FIG. 12 is an explanatory diagram illustrating an example of a process executed by a subjective assessment acquisition unit.

(Image presentation example 1) illustrated in FIG. 12 is an example in which the high-quality image 01-1 (IMG 01-1) (=HDR image) is displayed on the display unit which is the stimulus presentation unit 101.

The images, the assessment target image and the standard image are alternately displayed at a predetermined period, for example, a frequency of 3 Hz.

An image presentation method is similar to the method described above with reference to FIG. 5, the assessment target image and the standard image with a given image quality are alternately displayed, and a process of changing the assessment target image in units of predetermined periods is executed.

That is, an image presentation frequency is 3 Hz and the assessment target image and the standard image are set to be displayed three times for 1 second.

Note that the setting of the image presentation frequency=3 Hz is exemplary and another frequency may be applied.

In the case of the image presentation frequency=3 Hz, the subject 180 observes the images, the alternately displayed assessment target image and standard image, at the frequency of 3 Hz.

The subject 180 executes subjective image quality assessment on the observed images.

For example, a subjective assessment value=a subjective assessment value of 1 to 5 is set. Here, 5 is a subjective assessment value set in an image which the subject feels a highest image quality and 1 is a subjective assessment value set in an image which the subject feels a lowest image quality.

The subjective assessment value is input, for example, through a manipulation of a keyboard or a mouse or detection of a visual line position and the input value is input to the subjective assessment acquisition unit 131 and is recorded on the subjective assessment recording unit 132.

The subjective assessment value is recorded as a subjective assessment value associated with the subject and each image.

The subjective assessment analysis unit 133 analyzes the responses of the subject recorded by the subjective assessment acquisition unit 132.

An analysis process example executed by the subjective assessment analysis unit 133 will be described with reference to FIGS. 13A and 13B.

Figures 13A, 13B:
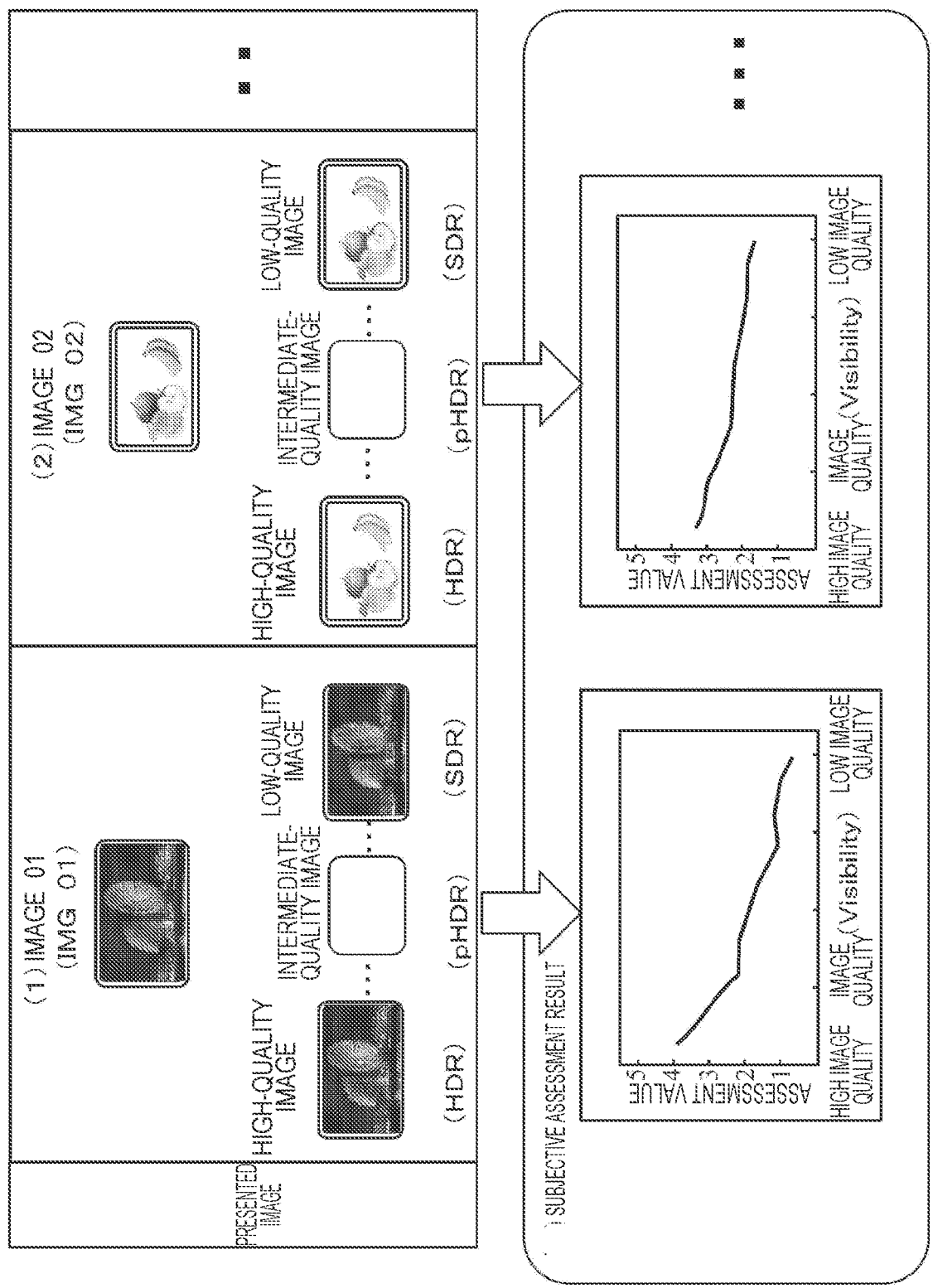
FIGS. 13A and 13B are explanatory diagrams illustrating an example of an analysis process executed by a subjective assessment analysis unit.

FIGS. 13A and 13B are diagrams illustrating an example of a subjective assessment result obtained on the basis of subjective assessment values (1 to 5) input by the subject in a case in which images with a plurality (10 kinds) of different image qualities in each of the images 01, 02, and the like configured from different display objects and the standard image are alternately displayed at the specific frequency (3 Hz).

In FIG. 13A presented images, images 01, 02, and the like configured from different display objects are shown. Images with a plurality (ten kinds) of image qualities are alternately displayed separately at 3 Hz with regard to each image. Then, the subject assesses the qualities of the observed images and inputs subjective assessment values.

In a subjective assessment result of FIG. 13B, a graph in which the image qualities are plotted on the horizontal axis and the subjective assessment values are plotted on the vertical axis is shown with regard to each of the images 01 and 02.

The horizontal axis represents image qualities (visibility levels) displayed on the display unit which is the stimulus presentation unit 101. The left side is set to indicate better image quality and the right side is set to indicate poorer image quality.

In an example illustrated in FIGS. 13A and 13B, in a case in which the image 01 configured from a night scene object is presented, a subjective assessment value of an HDR image is about 4.0 and a subjective assessment value of an SDR image is about 0.7.

In addition, in a case in which the image 02 configured from a fruit object is presented, a subjective assessment value of an HDR image is about 3.2 and a subjective assessment value of an SDR image is about 1.2.

Note that the subjective assessment values are also output to the result integration unit 141 or are stored in the storage unit in association with the subject and the images as in the brainwave signal.

[5. Process Executed by Result Integration Unit]

Next, the details of a process executed by the result integration unit 141 of the assessment model construction device 100 illustrated in FIG. 1 will be described.

The process executed by the result integration unit 141 will be described with reference to FIG. 14.

The result integration unit 141 integrates the brainwave analyzed by the brainwave analysis unit 123 and the subjective assessment analyzed by the subjective assessment analysis unit 133 in association therewith and stores integrated data in the storage unit or outputs the integrated data to the model construction unit 150.

The integrated data generated by the result integration unit 141 is data corresponding to the brainwave and the subjective assessment when a stimulus is presented to the subject 180 and is data equivalent to learning data to be used in the model construction unit 150 in the later section.

FIG. 14 is an explanatory diagram illustrating a process executed by the result integration unit 141.

FIG. 14 illustrates each of the following data:

(A) a brainwave analysis result corresponding to each image of each subject generated in the brainwave analysis unit 123;

(B) a subjective assessment result corresponding to each image of each subject generated in the subjective assessment analysis unit 133; and (C) integrated data generated in the result integration unit 141.

As illustrated in FIG. 14, the result integration unit 141 integrates the following data:

(A) a brainwave analysis result corresponding to each image of each subject generated in the brainwave analysis unit 123 (=objective assessment result); and (B) a subjective assessment result corresponding to each image of each subject generated in the subjective assessment analysis unit 133.

The result integration unit 141 stores the integrated data as data in which the brainwave analysis result and the subjective assessment result corresponding to each image of each subject are collected in the storage unit 201.

That is, the result integration unit 141 stores data in which the following data is associated with each other as the integrated data in the storage unit 201:

the subject—the image—the brainwave analysis result—the subjective assessment result.

The integrated data, that is, each subject, the brainwave analysis result corresponding to each image, and the subjective assessment result, are used as learning data in a machine learning process of constructing an image quality assessment model executed in the model construction unit 150.

[6. Details of Process Executed by Model Construction Unit]

Next, the details of a process executed by the model construction unit 150 of the assessment model construction device 100 illustrated in FIG. 1 will be described.

Figure 15:
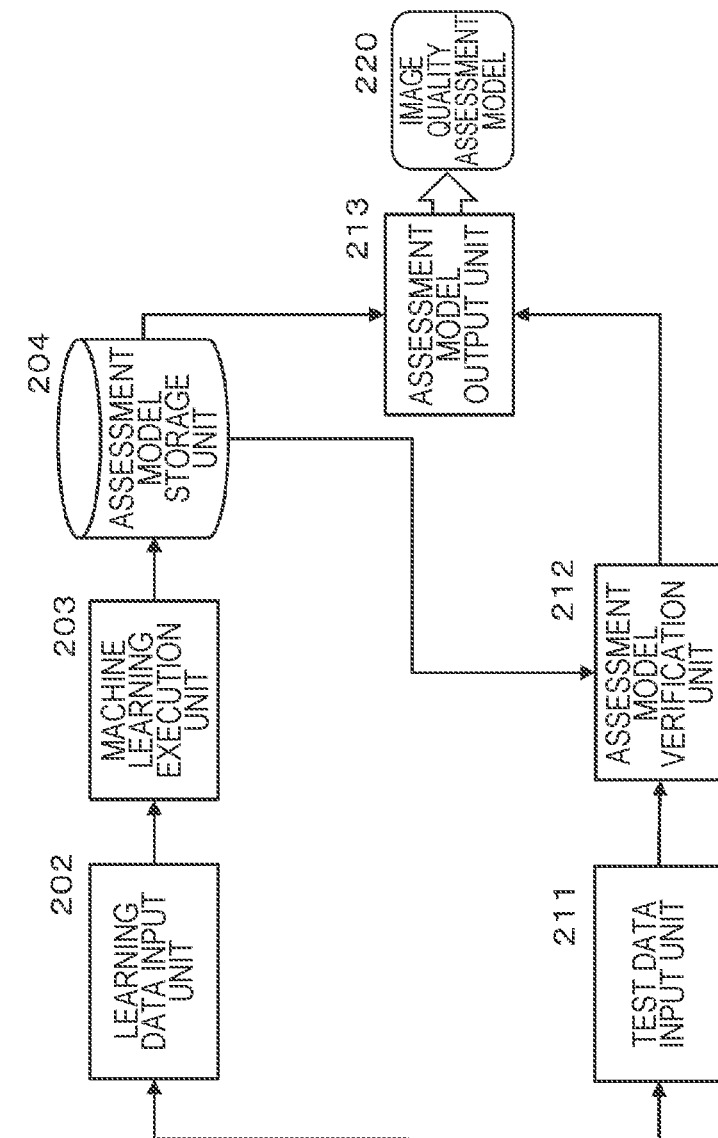
FIG. 15 is an explanatory diagram illustrating a configuration example of a model construction unit.

A configuration example of the model construction unit 150 is illustrated in FIG. 15.

The model construction unit 150 executes a machine learning process using the integrated data generated by the result integration unit 140:

(A) the brainwave analysis result corresponding to each image of each subject generated in the brainwave analysis unit 123; and (B) the subjective assessment result corresponding to each image of each subject generated in the subjective assessment analysis unit 133, that is, the integrated data in which the following data is associated with each other to construct an image quality assessment model:

the subject—the image—the brainwave analysis result—the subjective assessment result.

That is, by associating a change in a brainwave appearing as a response of a result obtained by presenting a stimulus to the subject who is an image observer with the subjective assessment of the subject to the presented stimulus, the image quality assessment model for enabling the image quality (the image quality as the subjective assessment result) of the image presented to the user to be assessed on the basis of the brainwave measurement result of the user (the subject) observing the image is constructed.

Specifically, the image quality assessment model for enabling whether the image presented to the user is an HDR image or an SDR image to be identified is constructed, for example, on the basis of the brainwave measurement result of the user (the subject) observing the image.

The model construction unit 150 constructs the image quality assessment model by executing machine learning using the integrated data generated in the result integration unit 141, that is, the integrated data in which the following data is associated with each other as learning data:

the subject—the image—the brainwave analysis result—the subjective assessment result.

The integrated data generated in the result integration unit 141 is stored in the storage unit 201 illustrated in FIG. 15.

A learning data input unit outputs the integrated data, that is, the integrated data in which the following data is associated with each other, from the storage unit 201 to a machine learning execution unit 203:

the subject—the image—the brainwave analysis result—the subjective assessment result.

The machine learning execution unit 203 constructs an image quality assessment model by executing the machine learning process using the integrated data.

Learning data applied to the machine learning process in the machine learning execution unit 203 includes student data and supervisor data. The machine learning execution unit 203 executes supervised machine learning.

Here, the student data is the brainwave analysis result, that is, data related to a feature amount of the brainwave and the supervisor data is a subjective assessment result.

The machine learning execution unit 203 executes the machine learning process using the learning data, constructs the image quality assessment model for enabling the qualities of the images presented to the user to be assessed on the basis of the brainwave measurement result of the user (subject) observing the images, and stores the image quality assessment model in an assessment model storage unit 204.

Note that an image quality assessment model construction process executed in the model construction unit 150 includes the following plurality of process steps:

(a) learning setting step;
(b) machine learning step;
(c) performance verification step; and
(d) assessment model output step.

The foregoing steps are included.

The (a) learning setting step and the (b) machine learning step are executed by the machine learning execution unit 203 illustrated in FIG. 15.

The (c) performance verification step is executed by an assessment model verification unit 212 illustrated in FIG. 15.

The (d) assessment model output step is executed by an assessment model output unit 213 illustrated in FIG. 15.

In the (a) learning setting step executed by the machine learning execution unit 203 illustrated in FIG. 15, selecting a machine learning algorithm, setting learning parameters, and shaping machine learning data in accordance to the machine learning algorithm are executed.

Specifically, as the machine learning algorithm, for example, there are various algorithms. For example, a support vector machine (SVM) can be used. Hereinafter, an example in which the support vector machine (SVM) is used will be described.

The support vector machine (SVM) is known as a supervised machine learning algorithm and can realize a high precise class classification process.

Note that in the supervised machine learning process of the example, the student data is a brainwave analysis result, that is, data related to a feature amount of the brainwave and the supervisor data is a subjective assessment result.

The class classification is a process of defining a predetermined number of classes to be classified and deciding (predicting) classes into which each piece of data is classified on the basis of the feature amounts of the data.

For example, classification target data is image data. The classified classes are, for example, two classes of a high-quality image class and a low-quality image class, specifically, two classes of an HDR image and an SDR image.

The feature amount is a brainwave analysis result.

The machine learning execution unit 203 executes the (b) machine learning step after the learning setting step is completed.

In the (b) machine learning step, a regression process or a classification process is executed on the input machine learning data on the basis of the setting of the learning setting step.

The pre-regression process is a process of predicting an output from the input data.

The classification process is a process of classifying input data into two or more categories.

For example, in a case in which the quality of an input stimulus (in this example, a presented image) is assessed, a regression model is constructed to predict quality or a classification model that has a plurality of categories is constructed to determine quality.

That is, the machine learning execution unit 203 constructs an image quality assessment model for executing a process of deciding (predicting) a class into which class observation target images are classified between a high-quality image class and a low-quality image class, specifically, two classes of an HDR image and an SDR image, using brainwave analysis results (feature amounts) of the user (the subject) observing the images.

The constructed image quality assessment model is stored in the assessment model storage unit 204.

Figure 16:
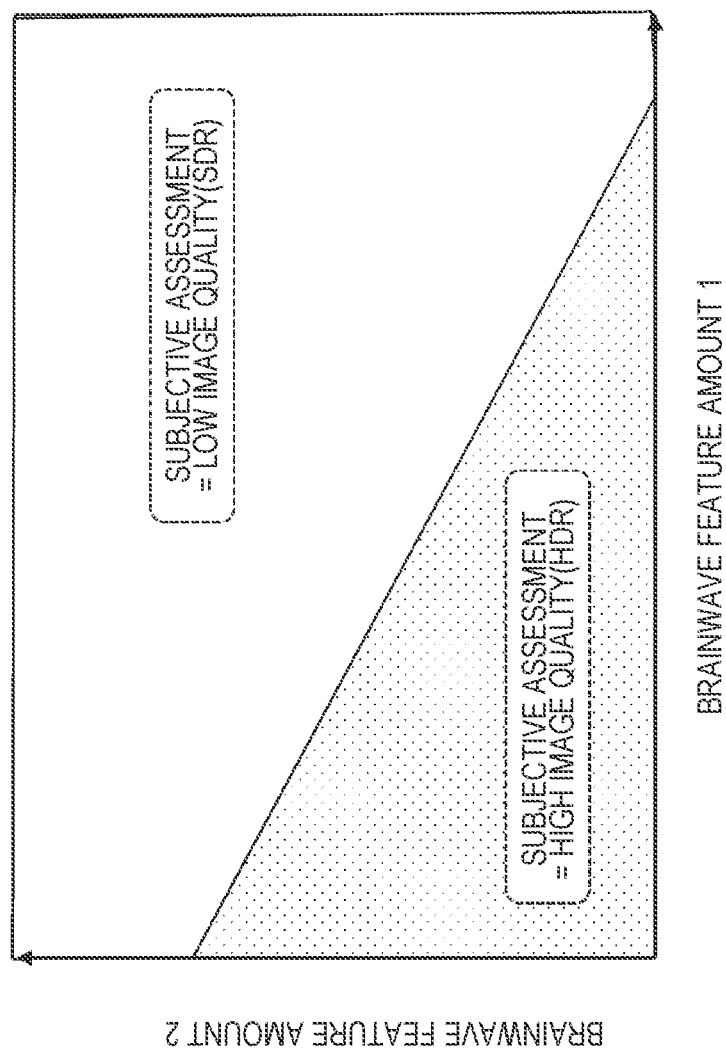
FIG. 16 is an explanatory diagram illustrating an example of an image quality assessment model generated by a machine learning execution unit.

The machine learning execution unit 203 constructs, for example, an image quality assessment model illustrated in FIG. 16.

The image quality assessment model illustrated in FIG. 16 is an image quality assessment model for enabling images to be classified into two classes on the basis of two different brainwave feature amounts.

That is, the image quality assessment model is an image quality assessment model for enabling images to be classified into the following two classes:

(first class) high-quality image class in which subjective assessment of an image observer is estimated to be a high-quality image (HDR); and (second class) low-quality image class in which subjective assessment of an image observer is estimated to be a low-quality image (SDR).

By applying the image quality assessment model, it is possible to estimate whether a presented image is a high-quality image (HDR) or a low-quality image (SDR) when a brainwave feature amount of the user (the subject) is acquired even in a case in which the user (the subject) is allowed to view an unknown image with a high image quality or a low image quality.

Note that in the image quality assessment model illustrated in FIG. 16, two brainwave feature amounts are used in this example. However, the number of brainwave feature amounts to be applied to the image quality assessment model may be set to be 1 or 3 or more. The specific example will be described later.

When the machine learning execution unit 203 constructs the image quality assessment model and the constructed image quality assessment model is stored in the assessment model storage unit 204, the process proceeds to the (c) performance verification step.

An assessment model performance verification unit 212 inputs the integrated data stored in the storage unit 201 as test data from the test data input unit 211 and executes performance verification of the image quality assessment model generated by the machine learning execution unit 203 using the test data.

Note that the integrated data used as the test data is assumed to be data which is not applied to a process of constructing the image quality assessment model in the machine learning execution unit 203.

The assessment model performance verification unit 212 verifies whether or not a class classification result obtained by applying the brainwave analysis result (the feature amount) included in the test data to the image quality assessment model generated by the machine learning execution unit 203 matches a subjective assessment result included in the test data (the integrated data).

When the class classification result matches the subjective assessment result, it is meant that correct class classification is executed by applying the image quality assessment model generated by the machine learning execution unit 203.

Conversely, when the class classification result does not match the subjective assessment result, it is meant that wrong class classification is executed by the image quality assessment model generated by the machine learning execution unit 203.

The assessment model performance verification unit 212 executes an assessment process in which, for example, an index such as an accuracy rate, precision, a reproduction ratio, or an F value which is generally known model assessment indexes is applied in the process of assessing the image quality assessment model generated by the machine learning execution unit 203.

In a case in which each of the index values indicates a value equal to or greater than a preset threshold in the process of assessing the image quality assessment model generated by the machine learning execution unit 203, performance of the image quality assessment model generated by the machine learning execution unit 203 is determined to be allowable performance and the process proceeds to the subsequent (d) assessment model output step.

Conversely, when predetermined performance is not satisfied, the process returns to the (a) learning setting step. Then, selecting a machine learning algorithm, setting learning parameters, and shaping machine learning data in accordance to the machine learning algorithm are again executed.

In a case in which the assessment model performance verification unit 212 determines that the performance of the image quality assessment model generated by the machine learning execution unit 203 is the allowable performance, the assessment model output unit 213 executes the (d) assessment model output step.

The assessment model output unit 213 outputs an image quality assessment model 220 assessed to have sufficient performance in the assessment model output step.

Figure 17:
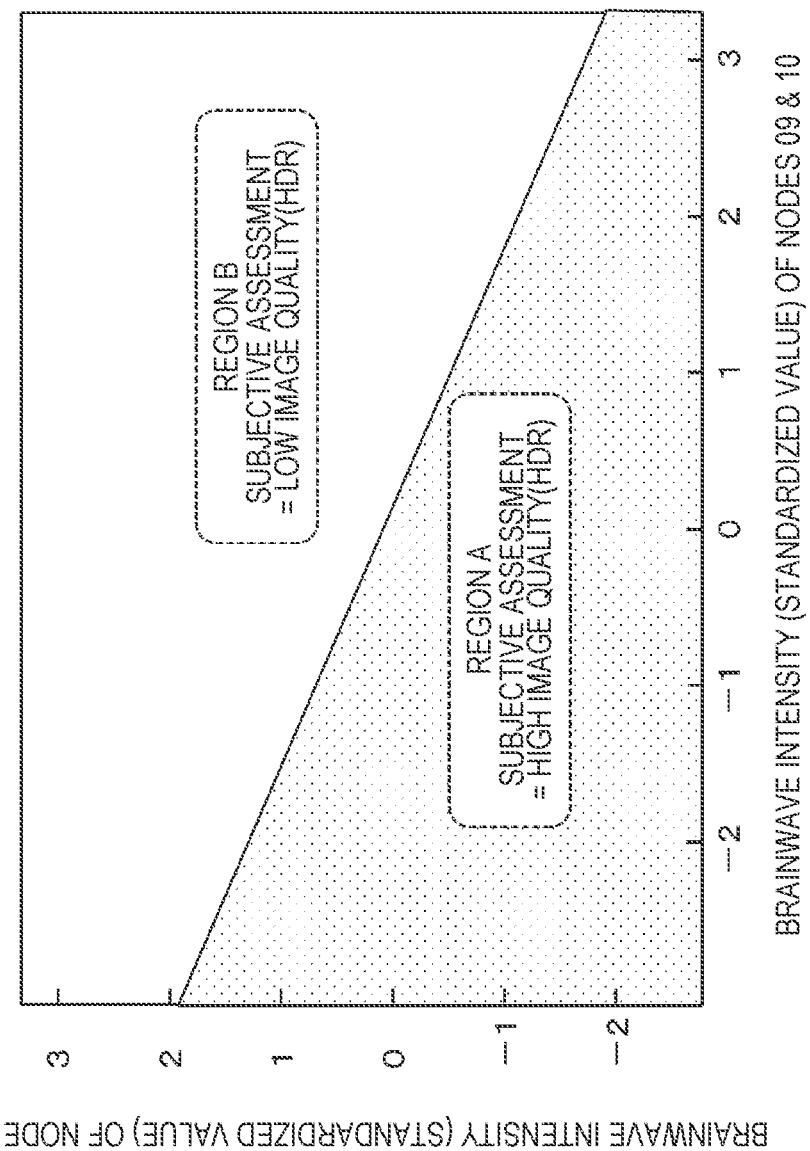
FIG. 17 is an explanatory diagram illustrating an example of an image quality assessment model generated by a machine learning execution unit.

One specific example of the image quality assessment model 220 output by the assessment model output unit 213 is illustrated in FIG. 17.

The image quality assessment model illustrated in FIG. 17 is a model in which the following two feature amounts are used as brainwave feature amounts to be applied to image quality estimation:

(feature amount 1) brainwave intensity (standardized value) of nodes (electrodes) 09 and 10; and (feature amount 2) brainwave intensity (standardized value) of a node (electrode) 20.

The nodes (electrodes) 09, 10, and 20 are nodes (electrodes) of the setting example of the brainwave measurement electrodes described above with reference to FIG. 3.

Note that a standardized value is a value after a conversion process of setting an average to 0 and setting the dispersion to 1 is executed.

As described above, the magnitude of a change in the potential of the brainwave itself differs for each subject since any of the ERP, the VEP, and the SSVEP is a signal weak in units of µV.

Therefore, even when the SSVEP is measured for a plurality of subjects under the same condition, there is a possibility of the intensity of the signal considerably varying. In this way, in a case in which an average or dispersion of the data group acquired under the same condition considerably differs for each subject, it is preferable to apply a scheme of applying a conversion process of setting the average to 0 and setting the dispersion to 1, which is referred to as data standardization. By standardizing the data, a variation between the subjects is absorbed and the data can be analyzed in the same criterion.

The image quality assessment model illustrated in FIG. 17 is a model for enabling quality (subjective assessment image quality) of an image observed by an image observing user to be estimated by detecting the following two brainwave feature amounts of the user observing the image.

(feature amount 1) brainwave intensity (standardized value) of nodes (electrodes) 09 and 10; and (feature amount 2) brainwave intensity (standardized value) of a node (electrode) 20.

When feature amount 1 (brainwave intensity of the nodes (electrodes) 09 and 10) and feature amount 2 (brainwave intensity of a node (electrode) 20) obtained from the brainwave measurement results of the user observing the images is within a range of a region A illustrated in FIG. 17, the quality (subjective assessment image quality) of the images observed by the image observing user can be estimated to be an image quality equivalent to an HDR image.

When feature amount 1 (brainwave intensity of the nodes (electrodes) 09 and 10) and feature amount 2 (brainwave intensity of a node (electrode) 20) obtained from the brainwave measurement results of the user observing the images is within a range of a region B illustrated in FIG. 17, the quality (subjective assessment image quality) of the images observed by the image observing user can be estimated to be an image quality equivalent to an SDR image.

The image quality assessment model 220 is an image quality assessment model for describing a quantitative relation between both the brainwave and the subjective assessment result derived by causing machine learning to be executed on a relation between the brainwave and the subjective assessment result.

By using the image quality assessment model 220, it is possible to estimate whether the quality of an image is, for example, a high quality or a low quality or the image is an HDR image or an SDR image on the basis of the brainwave signal of the user (the subject) observing the image.

That is, by allowing the user (the subject) to observe an image with an unknown image quality, measuring a brainwave of the user, calculating a brainwave feature amount corresponding to a brainwave feature amount set in the image quality assessment model 220, and applying the calculated brainwave feature amount to the image quality assessment model 220, it is possible to estimate whether the quality of the image is, for example, a high quality or low quality or the image is an HDR image or an SDR image.

Note that, for example, the image quality assessment model illustrated in FIG. 17 is a model for executing binary determination of the high image quality (HDR) and the low image quality (SDR), but the image quality assessment model can be set variously so that two kinds of class classification illustrated in FIG. 16 are executed.

For example, a determination result obtained by applying the image quality assessment model may be a binary format of 0 or 1 or Yes or No. Additionally, various classification results in accordance with a format of the constructed assessment model such as scores expressed as 0 to 100 can be output.

In addition, two kinds of feature amounts are used for the image quality assessment model illustrated in FIG. 17 and the image quality assessment model is set 2-dimensionally. For example, as illustrated in FIGS. 18A, 18B, and 18C, only one brainwave feature amount applied to the image quality assessment model may be used or three or more brainwave feature amounts may be set.

Figure 18A:
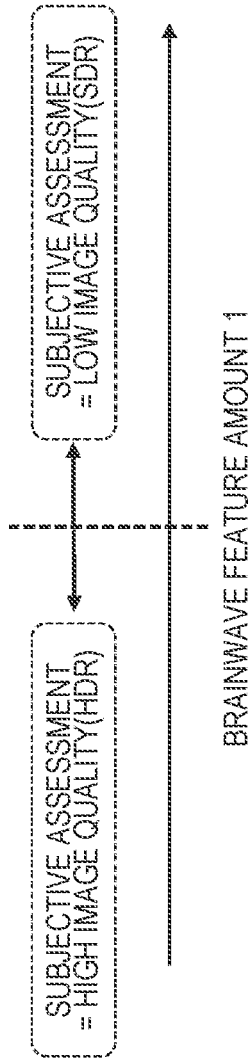
FIGS. 18A and 18B are explanatory diagrams illustrating an example of an image quality assessment model generated by a machine learning execution unit.

FIG. 18A illustrates an example of a 1-dimensional image quality assessment model in which one brainwave feature amount is used.

Figure 18B:
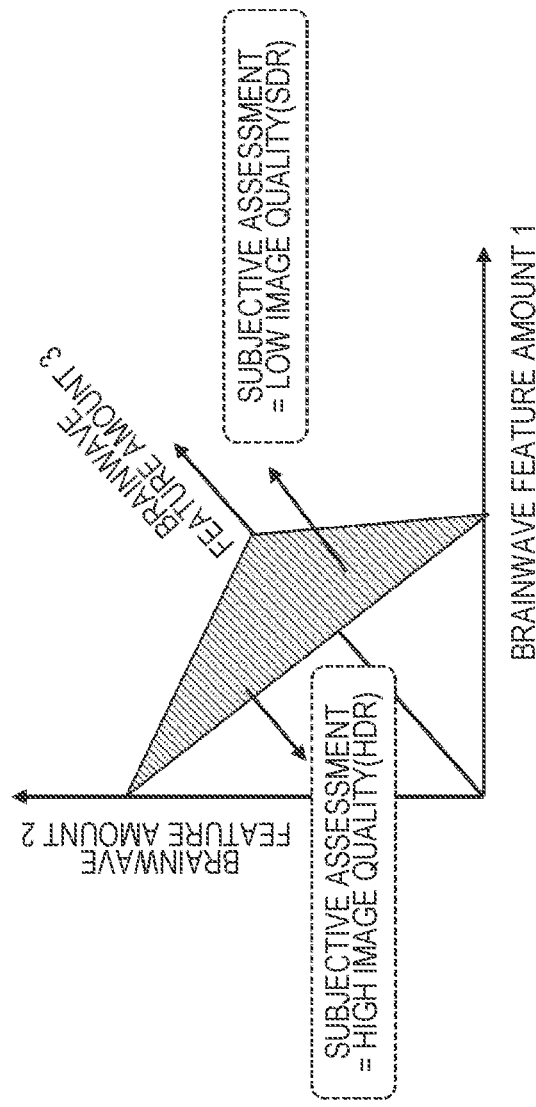

FIG. 18B illustrates an example of a 3-dimensional image quality assessment model in which three brainwave feature amounts are used.

Note that various feature amounts obtained from the brainwave measurement result can be used as feature amounts set in the image quality assessment model.

For example, in an electrode disposition example for brainwave measurement illustrated in FIG. 3, a "predetermined signal component" calculated from a "measurement signal of a predetermined electrode" can be used.

The "measurement signal of the predetermined electrode" includes, for example, the following signals:

(a) measurement signal obtained from one or more electrodes at any position; and (b) measurement signal obtained by compressing the number of dimensions by compressing the number of signal acquisition electrode dimensions (32 in the case of all the electrodes) through independent component analysis or the like in a case in which measurement signals are acquired from a plurality of electrodes or all the electrodes.

In addition, the "predetermined signal component" includes, for example, the following signal components:

(a) intensity component of the image presentation frequency (3 Hz in the example described with reference to FIG. 5 and the other drawings) or the secondary or tertiary harmonic (6 Hz, 9 Hz, or the like);

(b) phase component of the image presentation frequency (3 Hz in the example described with reference to FIG. 5 and the other drawings) or the secondary or tertiary harmonic (6 Hz, 9 Hz, or the like); and (c) a signal component (for example, an added average, a weight-added result, or the like) calculated by integrating the intensity components of a plurality of frequencies of the signal components acquired from the plurality of electrodes.

The assessment model construction device according to the above-described present disclosure is configured to construct an assessment model for enabling objective assessment which does not deviate from a subjective assessment result to be executed by associating a change in a brainwave appearing as a response of a result obtained by presenting a stimulus (an image or the like) to a subject who is an image observer with subjective assessment of the subject to the presented stimulus (the image or the like).

By executing image quality assessment based on a brainwave using the assessment model, it is possible to acquire an objective assessment result of an image quality which does not deviate from the subjective assessment.

Note that in the above-described embodiment, the example in which the images are used as stimuli to be presented to the subject, the images with the plurality of different image qualities of the HDR image to the SDR image with different dynamic ranges are presented to the subject, the brainwaves and the subjective assessment of the subject are acquired, and the image quality assessment model is constructed has been described.

In the configuration according to the present disclosure, images with image qualities other than the dynamic ranges, specifically, for example, different image qualities in accordance with the number of pixels such as high-precise images with a large number of pixels such as 4K or 8K and normal images with a smaller number of pixels than a 4K or 8K image, such as 2K, can be presented to the subject, brainwaves and subjective assessment of the subject can be acquired, and an image quality assessment model can also be constructed.

Further, for example, the subject can be allowed to hear sound data with a plurality of different sound qualities as well as viewing the images, brainwaves and subjective assessment of the subject can be acquired, and a sound quality assessment model can be constructed as well.

By executing sound quality assessment based on the brainwaves using the sound quality assessment model, it is possible to acquire an objective assessment result of sound quality which does not deviate from the subjective assessment.

[7. Process Sequence Executed by Information Processing Device]

Next, an execution sequence of an assessment model construction process executed by the assessment model construction device 100 illustrated in FIG. 1 will be described with reference to flowcharts illustrated in FIGS. 19 and 20.

Note that the assessment model construction device 100 illustrated in FIG. 1 includes a data processing unit that includes a CPU having a program execution function. Processes in accordance with the flowcharts illustrated in FIGS. 19 and 20 are executed under the control of the data processing unit. Note that a hardware configuration example of the information processing device will be described in a later section.

The assessment model construction process executed by the assessment model construction device 100 illustrated in FIG. 1 can broadly be divided into the following four steps:

(A) preparation step;
(B) presentation and measurement step;
(C) analysis step; and
(D) model construction step.

The four steps are included.

Hereinafter, a detailed process of each step will be described.

(A) Preparation Step

Figure 19:
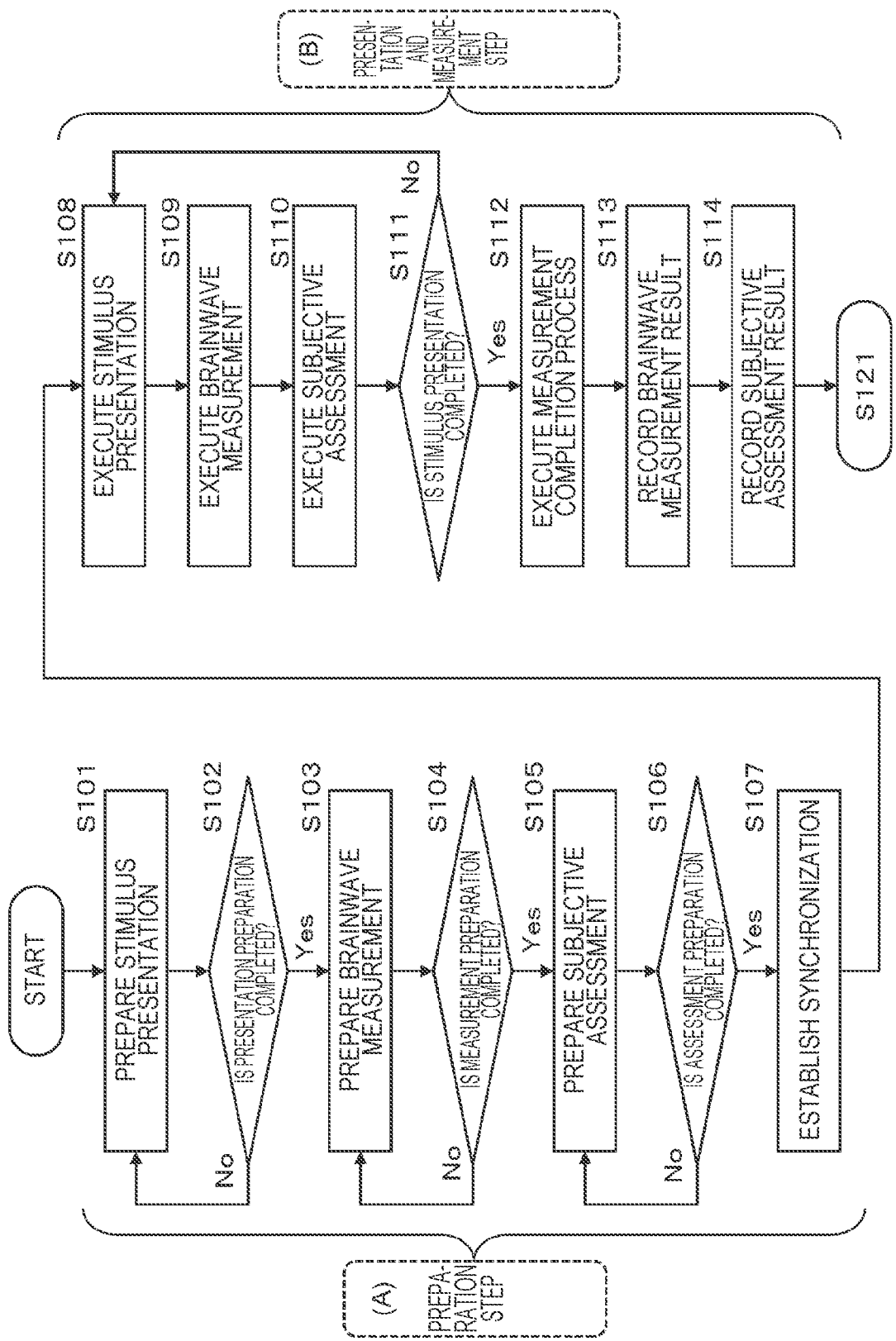
FIG. 19 is a diagram illustrating a flowchart for describing an execution sequence of an assessment model construction process executed by an assessment model construction device.

The preparation step is a process of steps S101 to S107 of the flowchart illustrated in FIG. 19. Hereinafter, the process of each step will be described.

(Steps S101 and S102)

In a stimulus presentation preparation step and a preparation completion checking step of steps S101 and S102, it is checked whether stimuli to be presented to the subject, specifically, images, are prepared or parameters such as an image output frequency of the stimulus presentation unit, that is, the display unit (the display), are set.

When the preparation is made, the process proceeds to a brainwave measurement preparation step of step S103.

(Steps S103 and S104)

In the brainwave measurement preparation step and a measurement preparation completion checking step of steps S103 and S104, it is checked whether hardware that acquires brainwaves of the subject is prepared and software is set.

When the preparation is made, the process proceeds to a subjective assessment acquisition preparation step of step S105.

(Steps S105 and S106)

In the subjective assessment acquisition preparation step and an assessment preparation completion checking step of steps S105 and S106, it is checked whether the subjective assessment of the subject to the presented stimulus can be acquired.

Note that it is sufficient if only the preparation step is executed in a case in which the brainwave measurement and the subjective assessment acquisition are not simultaneously executed.

When the preparation until here is completed, the process proceeds to a synchronization establishment step of step S107.

(Step S107)

In the synchronization establishment step of step S107, a synchronization operation is executed during the stimulus presentation, the brainwave measurement, and the subjective assessment acquisition.

This is executed to determine later a stimulus to which the brainwave responds, a time relation between the change in the brainwave and a presentation time of the stimulus, and a stimulus to which the subjective assessment is executed.

(B) Presentation and Measurement Step

The presentation and measurement step is a process of steps S108 to S114 of the flowchart illustrated in FIG. 19. Hereinafter, the process of each step will be described.

(Step S108)

In the stimulus presentation step of step S108, stimuli prepared in advance (in this example, alternate display of the assessment target images and the standard images) are presented to the subject in accordance with a predetermined rule.

For example, the alternate display of 3 Hz is executed.

(Step S109)

In the brainwave measurement step of step S109, brainwaves of the subject to the presented stimuli (in this example, the alternate display of the assessment target images and the standard images) are measured.

For example, a brainwave measurement process is executed using the electrodes set at the electrode setting positions illustrated in FIG. 3.

(Step S110)

In the subjective assessment acquisition step of step S110, the subjective assessment of the subject to the presented stimuli is acquired.

Note that in a case in which the brainwave measurement and the subjective assessment acquisition are not simultaneously executed, it is sufficient if any of the brainwave measurement step and the subjective assessment acquisition step is executed.

(Step S111)

In step S111, when it is checked that the predetermined stimuli (in this example, the image presentation process) are all presented, the process proceeds to an ending process step of step S112.

(Step S112)

In the ending process step of step S112, a process of disconnecting the earlier established synchronization, a process of storing the data of the acquired brainwave or the measured subjective assessment in the storage unit, or the like is executed.

(Step S113)

In a brainwave day measurement result recording step of step S113, the brainwaves measured in the brainwave measurement step of step S109 is recorded as the data.

For example, the brainwave signal recording process described above with reference to FIGS. 8A 8B, 9A, and 9B is executed.

(Step S114)

In the subjective assessment result recording step of step S114, the subjective assessment result acquired in the subjective assessment acquisition step of step S110 is recorded as data.

For example, the subjective assessment values of the image qualities by the user (the subject) are recorded as 5-stage assessment values or the like of 1 to 5.

When the recording of all the data is completed, the process proceeds to a subsequent analysis step.

(C) Analysis Step

Figure 20:
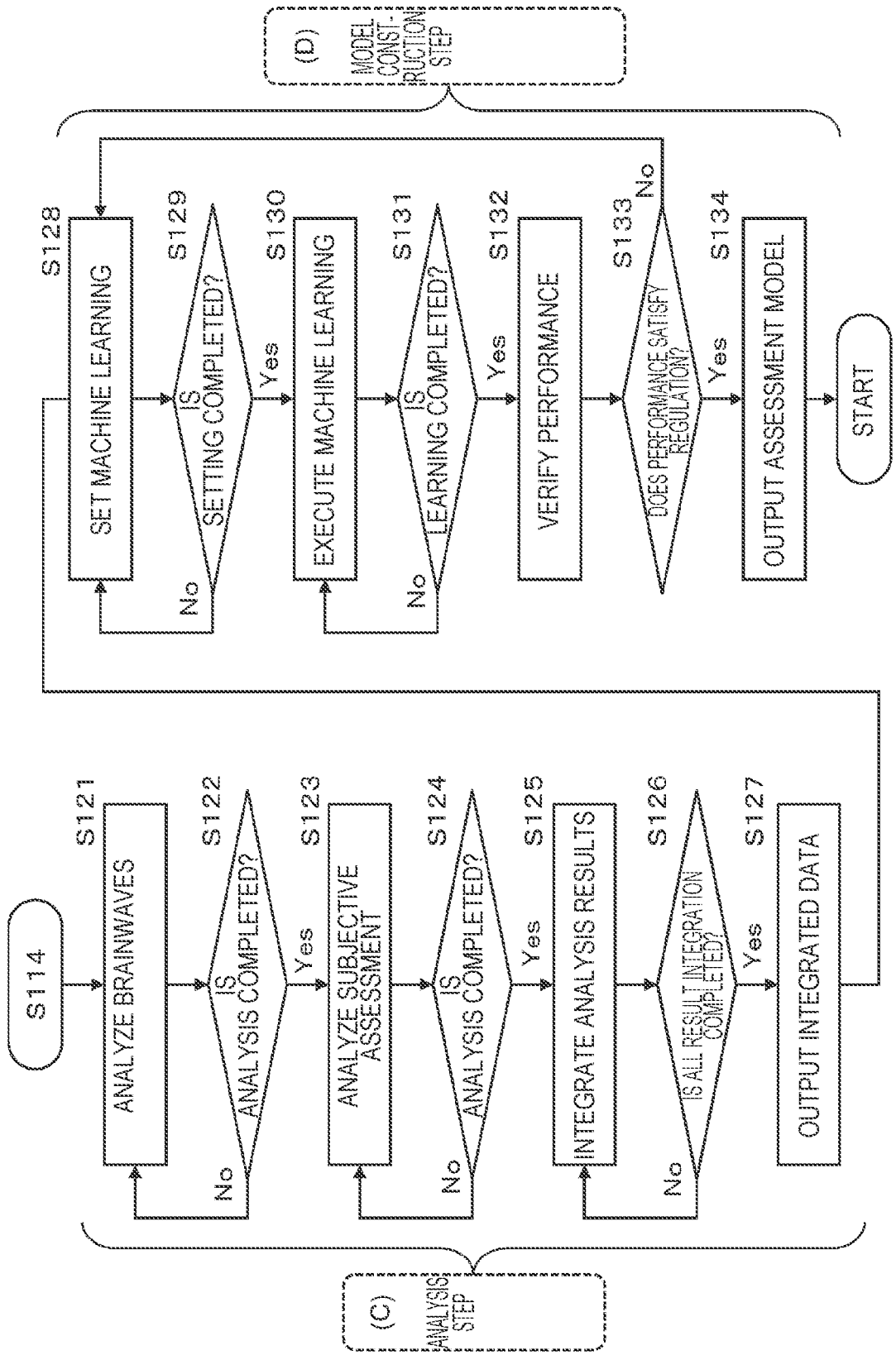
FIG. 20 is a diagram illustrating a flowchart for describing an execution sequence of an assessment model construction process executed by an assessment model construction device.

The analysis step is a process of steps S121 to S127 of the flowchart illustrated in FIG. 20. Hereinafter, the process of each step will be described.

(Steps S121 and S122)

In a brainwave analysis step of step S121, the brainwaves recorded in the brainwave measurement result recording step of step S113 are analyzed in accordance with an appropriate method.

As described above, in a case in which the measured brainwaves are the ERP or the VEP, the analysis at the spatial axis, the time axis, and the frequency axis is executed in many cases. In a case in which the measured brainwaves are the SSVEP, the analysis at the frequency axis is executed in many cases.

Note that before the analysis, it is preferable to apply a filtering process by a bandpass filter or a notch filter to the recorded brainwaves in order to remove an unnecessary signal or suppress noise.

Through the brainwave analysis process, for example, analysis results of the detection intensity signal Si, the brainwave intensity signal Fi, and the like of the brainwaves described with reference to FIGS. 10 and 11 are generated.

Note that the brainwave analysis data is generated as analysis data in which the subject and each image are associated with each other.

When the completion of the brainwave analysis is checked in step S122, the process proceeds to a subjective assessment analysis step of step S123.

(Steps S123 and S124)

In the subjective assessment analysis step of step S123, the subjective assessment result recorded in the subjective assessment result recording step of step S114 is analyzed in accordance with an appropriate method.

For example, in a case in which the same stimulus is presented a plurality of times, an average value, a mode, or a median value of scores is considered to be calculated.

Through the subjective assessment result analysis process, for example, the subjective assessment result described with reference to FIGS. 13A and 13B is generated.

Note that the subjective assessment result is also generated as data in which the subject and each image are associated with each other, as in the brainwave analysis data.

In step S124, when the completion of the subjective assessment analysis is checked, the process proceeds to an analysis result integration step of step S125.

(Steps S125 and S126)

In the analysis result integration step of step S125, the separate brainwave analysis result and subjective assessment analysis result are integrated in association with the subject and the images.

This process is the process executed by the result integration unit 141 described above with reference to FIG. 14.

As illustrated in FIG. 14, the result integration unit 141 integrates the following data:

(A) a brainwave analysis result corresponding to each image of each subject generated in the brainwave analysis unit 123; and (B) a subjective assessment result corresponding to each image of each subject generated in the subjective assessment analysis unit 133.

The result integration unit 141 stores the integrated data as data in which the brainwave analysis result and the subjective assessment result corresponding to each image of each subject are collected in the storage unit.

That is, the result integration unit 141 stores data in which the following data is associated with each other as the integrated data in the storage unit:

the subject—the image—(the brainwave analysis result, the subjective assessment result).

When it is checked that the analysis results are all integrated in step S126, the process proceeds to an integrated data output step of step S127.

(Step S127)

In the integrated data output step of step S127, the integrated analysis result is output as machine learning data to the model construction unit of the assessment model construction device 100 illustrated in FIG. 1 and the process proceeds to the model construction step.

(D) Model Construction Step

The model construction step is a process of steps S128 to S134 of the flowchart illustrated in FIG. 20. Hereinafter, the process of each step will be described.

(Steps S128 and S129)

In the machine learning setting step of step S128, selecting a machine learning algorithm, setting learning parameters, and shaping machine learning data in accordance to the machine learning algorithm are executed.

For example, a support vector machine (SVM) known as the above-described supervised machine learning algorithm is selected as the machine learning algorithm.

Further, a process of setting the brainwave analysis result, that is, the data related to the feature amount of the brainwaves, as student data and setting the subjective assessment result as supervisor data, or the like is executed.

When the setting completion is checked in step S129, the process proceeds to a machine learning step of step S130.

(Steps S130 and S131)

In the machine learning step of step S130, the machine learning process is executed on the input machine learning data on the basis of the setting in the machine learning setting step of step S128. For example, a machine learning process accompanying regression and classification is executed.

Note that, as described above, an output from the input data is predicted in the regression. The classification is classification of the input data into two or more categories.

For example, in a case in which the quality (for example, high quality (HDR) or low quality (SDR)) of an input stimulus (in this example, an image) is assessed, a regression model is constructed to predict quality or a classification model that has a plurality of categories is constructed to determine quality.

The process executed in the machine learning step of step S130 is the process described above with reference to FIGS. 15, 16, 17, 18A and 18B and is specifically the following process.

That is, an image quality assessment model for executing a process of deciding (predicting) a class into which class observation target images are classified between a high-quality image class and a low-quality image class, specifically, two classes of an HDR image and an SDR image is constructed using brainwave analysis results (feature amounts) of the user (the subject) observing the images.

The constructed image quality assessment model is stored in the assessment model storage unit 204 illustrated in FIG. 15.

In the machine learning step of step S130, the machine learning execution unit 203 illustrated in FIG. 15 constructs, for example, the image quality assessment model illustrated in FIG. 16.

When the completion of the machine learning is checked in step S131, the process proceeds to a performance verification step of step S132.

(Steps S132 and S133)

In the performance verification step of step S132, the performance of the assessment model constructed in the machine learning step of step S130 is assessed.

As the assessment index, an accuracy rate, precision, a reproduction ratio, an F value, or the like of the model is used.

This process is a process executed by the assessment model verification unit 212 illustrated in FIG. 15.

As described above, the assessment model performance verification unit 212 verifies whether or not a class classification result obtained by applying the brainwave analysis result (the feature amount) included in the test data to the image quality assessment model generated by the machine learning execution unit 203 matches a subjective assessment result included in the test data (the integrated data).

When the class classification result matches the subjective assessment result, it is meant that correct class classification is executed by applying the image quality assessment model generated by the machine learning execution unit 203.

Conversely, when the class classification result does not match the subjective assessment result, it is meant that wrong class classification is executed by the image quality assessment model generated by the machine learning execution unit 203.

In a case in which it is checked that the generated assessment model satisfies predetermined performance in step S133, the process proceeds to the assessment model output step of step S134.

Conversely, when predetermined performance is not satisfied, the process returns to the machine learning setting step of step S128. Then, selecting a machine learning algorithm, setting learning parameters, and shaping machine learning data in accordance with the machine learning algorithm are again executed.

(Step S134)

In the assessment model output step of step S134, the image quality assessment model assessed to have sufficient performance is output.

This process is a process executed by the assessment model output unit 213 illustrated in FIG. 15, as described above.

The image quality assessment model 220 output by the assessment model output unit 213 is, for example, the image quality assessment model described above with reference to FIG. 17.

The image quality assessment model generated in accordance with the above-described sequence is a model in which the change in the brainwave appearing as the response of the result obtained by presenting the image to the subject who is an image observer is associated with the subjective assessment of the subject to the presented image, and is an image quality assessment model for realizing objective assessment which does not deviate from the subjective assessment result.

By executing image quality assessment based on a brainwave using the assessment model, it is possible to acquire an objective assessment result of an image quality which does not deviate from the subjective assessment.

Note that the above-described sequence is a sequence in which the subjective assessment process is executed along with the brainwave measurement process, but the brainwave measurement process and the subjective assessment process can also be executed separately.

In this case, steps S105, S106, S114, S123 and S124 related to the subjective assessment process are executed as processes separate from the brainwave measurement process. Thereafter, the process subsequent to step S125 may be configured to be executed using results of the two processes.

[8. Configuration and Process of Assessment Model Application Image Quality Assessment Device]

Next, a configuration and a process of an assessment model application image quality assessment device which is an information processing device that executes image quality determination using the image quality assessment model generated through the machine learning process by the assessment model construction device 100 described with reference to FIG. 1 and the subsequent drawings will be described.

Figure 21:
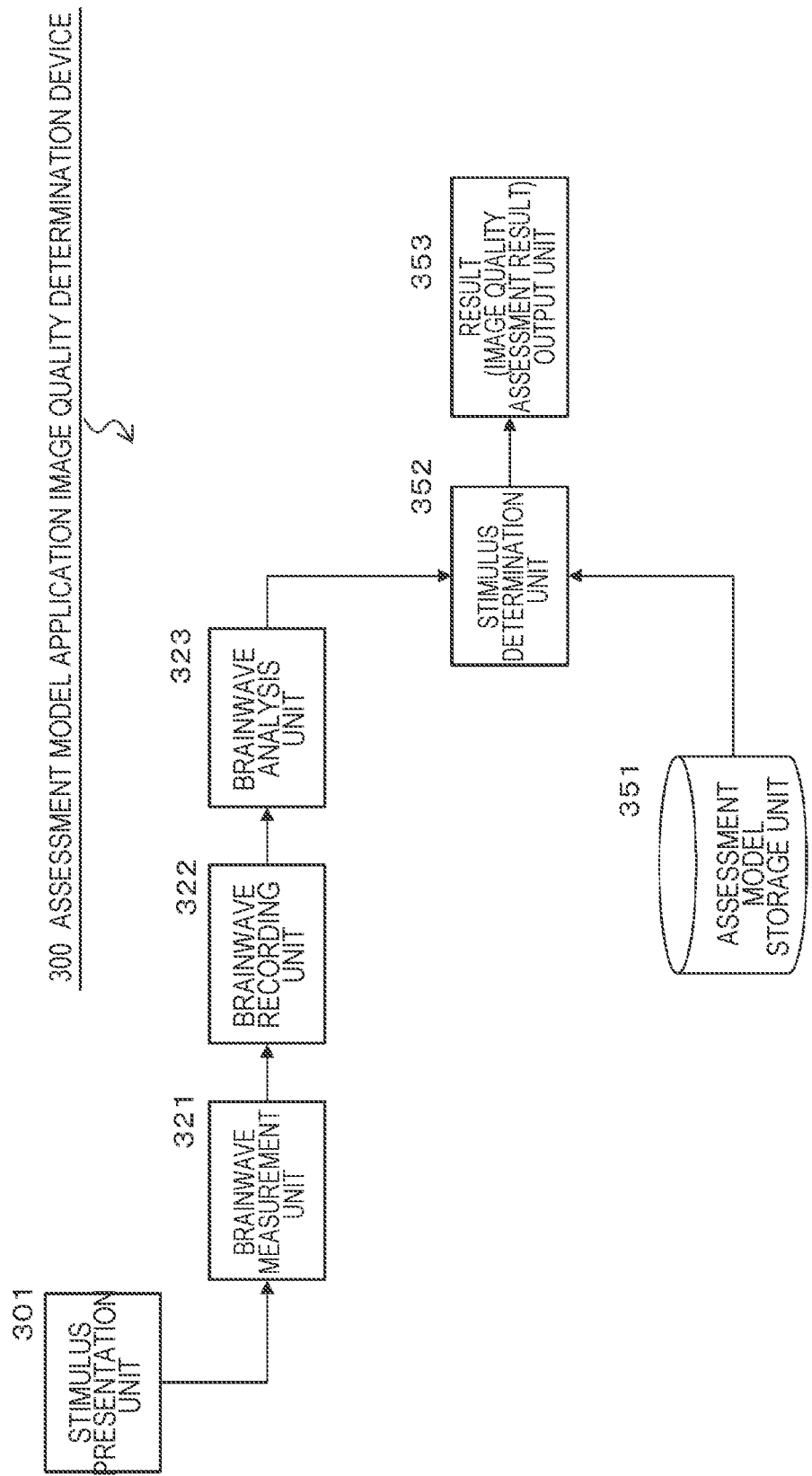
FIG. 21 is a block diagram illustrating a configuration example of an assessment model application image quality determination device.

FIG. 21 is a block diagram illustrating a configuration example of an assessment model application image quality determination device 300.

The assessment model application image quality determination device 300 illustrated in FIG. 21 stores an image quality assessment model which is the assessment model generated through the machine learning process by the assessment model construction device 100 described with reference to FIG. 1 and the subsequent drawings in the assessment model storage unit 351.

For example, the image quality assessment model described with reference to FIG. 17 is stored in the assessment model storage unit 351.

The assessment model application image quality determination device 300 executes a process of identifying whether an image presented to the user (the subject) is a high-quality image such as an HDR image or a low-quality image such as an SDR image by using the image quality assessment model stored in the assessment model storage unit 351.

In the identifying process, an analysis signal of a brainwave of the user (the subject) observing an identification target image is used.

That is, for example, in a case in which the process using the image quality assessment model illustrated in FIG. 17 is executed, the same feature amounts as the two brainwave feature amounts set in the image quality assessment model illustrated in FIG. 17, that is, two feature amounts are generated from the brainwaves of the user (the subject).

(feature amount 1) brainwave intensity (standardized value) of nodes (electrodes) 09 and 10; and (feature amount 2) brainwave intensity (standardized value) of a node (electrode) 20.

Further, it is determined whether values of the generated two feature amounts are included in the region A (the high-quality (HDR)) or the region B (the low-quality (SDR)) of the image quality assessment model illustrated in FIG. 17.

On the basis of the determination result, it is identified whether the image presented to the user (the subject) is a high-quality image such as an HDR image or a low-quality image such as an SDR image.

A configuration and a process of the assessment model application image quality determination device 300 illustrated in FIG. 21 will be described.

As illustrated in FIG. 21, the assessment model application image quality determination device 300 includes a stimulus presentation unit 301, a brainwave measurement unit 321, a brainwave recording unit 322, a brainwave analysis unit 323, an assessment model storage unit 351, a stimulus determination unit 352, and a result (image quality assessment result) output unit 353.

The stimulus presentation unit 301 presents a stimulus to the subject from the outside as in the stimulus presentation unit 101 of the assessment model construction device 100 described above with reference to FIG. 1.

Specifically, a visual stimulus such as an image or a video or an auditory stimulus such as a sound or music is presented.

A scheme for a stimulus to be presented is any of the following schemes such as the stimulus presentation unit 101 of the above-described assessment model construction device 100.

(a) an event-related potential (ERP) measurement scheme;

(b) a visual evoked potential (VEP) measurement scheme; and (c) a steady-state visual evoked potential (SSVEP) measurement scheme.

Here, the same scheme as the scheme used in the process of constructing the image quality assessment model is assumed to be used.

For example, images, an assessment target image and a standard image, are alternately displayed on the display unit at a predetermined period, for example, a frequency of 3 Hz.

That is, the image presentation frequency is 3 Hz and the assessment target image and the standard image are alternately displayed three times for 1 second.

The brainwave measurement unit 321 measures a change in potential on the scalp of the subject through the electrodes worn on the head of the subject as in the brainwave measurement unit 121 of the assessment model construction device 100 described above with reference to FIG. 1.

The disposition of the electrodes is the same as the disposition of the electrodes used when the model is constructed. For example, the electrode disposition described above with reference to FIG. 3 is assumed to be used.

The brainwave recording unit 322 records brainwaves of the subject acquired by the brainwave measurement unit 321 as in the brainwave recording unit 122 of the assessment model construction device 100 described above with reference to FIG. 1.

Note that since the brainwave is an analog signal, the brainwave is subjected to analog-digital (AD) conversion and is recorded as a digital signal in the brainwave recording unit 322.

The brainwave analysis unit 323 analyzes the brainwaves of the subject recorded by the brainwave recording unit 322 as in the brainwave analysis unit 123 of the assessment model construction device 100 described above with reference to FIG. 1.

As described above, in a case in which the measured brainwaves are the ERP or the VEP, the analysis at the spatial axis, the time axis, and the frequency axis is executed in many cases. In a case in which the measured brainwaves are the SSVEP, the analysis at the frequency axis is executed in many cases.

Note that before the analysis, it is preferable to apply a filtering process by a bandpass filter or a notch filter to the recorded brainwaves in order to remove an unnecessary signal or suppress noise.

Note that in the brainwave analysis process, a process of acquiring the same feature amounts as the brainwave feature amounts set in the image quality assessment model stored in the assessment model storage unit 351 is executed.

For example, in a case in which the image quality assessment model stored in the assessment model storage unit 351 is the image quality assessment model illustrated in FIG. 17, the same feature amounts as the two brainwave feature amounts set in the image quality assessment model illustrated in FIG. 17 are generated from the brainwaves of the user (the subject). That is, the following two feature amounts are generated.

(feature amount 1) brainwave intensity (standardized value) of nodes (electrodes) 09 and 10; and (feature amount 2) brainwave intensity (standardized value) of a node (electrode) 20.

The stimulus determination unit 352 determines an image quality region (class) of the image quality assessment model to which the region corresponding to the feature amount corresponds by applying the analysis result of the brainwaves of the image observer generated by the brainwave analysis unit 323, that is, the same feature amounts as the brainwave feature amounts set in the image quality assessment model stored in the assessment model storage unit 351, to the assessment model read from the assessment model storage unit 351.

For example, in a case in which the image quality assessment model stored in the assessment model storage unit 351 is the image quality assessment model illustrated in FIG. 17, it is determined whether the values of the feature amounts acquired as the brainwave analysis result of the image observer are included in the region A (the high quality (HDR)) or the region B (the low quality (SDR)) of the image quality assessment model illustrated in FIG. 17.

On the basis of the determination result, it is determined whether the image presented to the user (the subject) is a high-quality image such as an HDR image or a low-quality image such as an SDR image.

The determination result is output from the result (image quality assessment result) output unit 353.

By applying the image quality assessment model in the manner described above, it is possible to estimate whether a presented image is a high-quality image (HDR) or a low-quality image (SDR) when a brainwave feature amount of the user (the subject) is acquired even in a case in which the user (the subject) is allowed to view an unknown image with a high image quality or a low image quality.

That is, it is possible to obtain the image quality assessment result which does not deviate from the subjective image quality assessment result of the user (the subject) through the objective image quality assessment process using the brainwave feature amounts of the user (the subject).

Note that, in the above-described embodiment, the example in which the model for determining the image quality of the HDR image to the SDR image with the different dynamic ranges is applied as the image quality assessment model has been described. As described above, an image quality assessment model for assessing image qualities other than the dynamic range, for example, image qualities in accordance with the number of pixels such as a high-precise images with a large number of pixels such as 4K or 8K or normal images or the like with a smaller number of pixels than a 4K or 8K image, such as 2K, can also be applied as the image quality assessment model.

Further, for example, by allowing the subject to hear sound data with a plurality of different sound qualities as well as viewing the images and executing sound quality assessment based on brainwaves using a sound quality assessment model generated by acquiring brainwaves and subjective assessment of the subject, it is also possible to acquire an objective assessment result of the sound qualities which does not deviate from the subjective assessment.

[9. Hardware Configuration Example of Information Processing Device]

Next, a configuration example of a hardware configuration of an information processing device configured as the assessment model construction device 100 described above with reference to FIG. 1 and the other drawings and the assessment model application image quality determination device 300 described above with reference to FIG. 21 will be described with reference to FIG. 22.

A central processing unit (CPU) 501 functions as a data processing unit that executes various processes in accordance with programs stored in a read-only memory (ROM) 502 or a storage unit 508. For example, the CPU 501 executes the processes in accordance with the sequences described in the above-described embodiments. A random access memory (RAM) 503 stores data or a program executed by the CPU 501. The CPU 501, the ROM 502, and the RAM 503 are connected to each other by a bus 504.

The CPU 501 is connected to an input and output interface 505 via the bus 504. An input unit 506 including any of various switches, a keyboard, a mouse, a microphone, or the like, an output unit 507 including a display, a speaker, or the like, are connected to the input and output interface 505. The CPU 501 executes various processes in response to instructions input from the input unit 506 and outputs processing results to, for example, the output unit 507.

The storage unit 508 connected to the input and output interface 505 includes, for example, a hard disk and stores various kinds of data or programs executed by the CPU 501. The communication unit 509 functions as a transceiver unit for data communication via a network such as the Internet or a local area network and further functions as a transceiver unit for broadcast waves to communicate with an external device.

A drive 510 connected to the input and output interface 505 drives a removable medium 511 such as a magnetic disk, an optical disc, a magneto-optical disc, or a semiconductor memory such as a memory card to execute data recording or reading.

[10. Summary of Configuration of Present Disclosure]

The foregoing thus provides a detailed explanation of embodiments of the present disclosure with reference to specific embodiments. However, it is obvious that persons skilled in the art may make modifications and substitutions to these embodiments without departing from the gist of the present disclosure. In other words, the present disclosure has been disclosed by way of example, and should not be interpreted in a limited manner. The gist of the present disclosure should be determined in consideration of the claims.

Additionally, the present technology may also be configured as below.

(1)

An information processing device including:
a brainwave analysis unit configured to measure a brainwave of a subject to which a stimulus is presented and calculate a brainwave feature amount;
a subjective assessment analysis unit configured to acquire a subjective assessment value with respect to the stimulus of the subject; and
a model construction unit configured to construct an assessment model representing relevance between the brainwave feature amount and the subjective assessment value.

(2)

The information processing device according to (1),
in which the brainwave analysis unit acquires brainwave feature amounts corresponding to image qualities obtained by presenting images with different image qualities to the subject, and
the subjective assessment analysis unit acquires subjective assessment values corresponding to the image qualities obtained by presenting the images with the different image qualities to the subject.

(3)

The information processing device according to (1) or (2), in which the model construction unit uses the brainwave feature amount and the subjective assessment value as input data and constructs an assessment model representing relevance between the brainwave feature amount and the subjective assessment value through machine learning using the input data as learning data.

(4)

The information processing device according to (3), in which the model construction unit uses the subjective assessment value as supervisor data and executes supervised machine learning using the brainwave feature amount as student data.

(5)

The information processing device according to (3) or (4), in which the model construction unit executes machine learning in which a support vector machine (SVM) is applied as a machine learning algorithm.

(6)

The information processing device according to (2), in which the images with the different image qualities include images with different dynamic ranges.

(7)

The information processing device according to any one of (1) to (6),
in which the presentation of the stimulus is executed as alternate presentation of an assessment target image and a standard image, and
the brainwave analysis unit acquires a brainwave feature amount on the basis of a change in a brainwave in accordance with a display period of the images.

(8)

The information processing device according to any one of (1) to (7), in which the brainwave analysis unit acquires steady-state visual evoked potential (SSVEP) from a brainwave of the subject and calculates the brainwave feature amount.

(9)

The information processing device according to (8),
in which the presentation of the stimulus is executed as alternate presentation of an assessment target image and a standard image, and the brainwave analysis unit analyzes intensity of the SSVEP of the subject in accordance with a display period of the images.

(10)

The information processing device according to any one of (1) to (9), in which the subjective assessment analysis unit acquires a subjective assessment value of the subject in accordance with a mean opinion score (MOS) scheme.

(11)

The information processing device according to any one of (1) to (10), in which the model construction unit constructs an assessment model for estimating a subjective assessment value from the brainwave feature amount.

(12)

The information processing device according to (11), in which the brainwave analysis unit calculates a plurality of different brainwave feature amounts, and the model construction unit constructs an assessment model for estimating a subjective assessment value from the plurality of different brainwave feature amounts.

(13)

An information processing device including:

a brainwave analysis unit configured to measure a brainwave of a subject to which a stimulus is presented and calculate a brainwave feature amount;

a storage unit configured to store an assessment model for enabling a subjective assessment value based on the brainwave feature amount to be acquired; and a stimulus determination unit configured to apply the assessment model to estimate the subjective assessment value from the brainwave feature amount of the subject.

(14)

The information processing device according to (13), in which the assessment model is an assessment model representing a correspondence relation between brainwave feature amounts corresponding to image qualities obtained by presenting images with different image qualities to the subject and subjective assessment values corresponding to the image qualities.

(15)

The information processing device according to (13) or (14), in which the assessment model is an image quality assessment model generated through supervised machine learning in which the subjective assessment values are used as supervisor data and the brainwave feature amounts are used as student data.

(16)

The information processing device according to any one of (13) to (15), in which the presentation of the stimulus is executed as alternate presentation of an assessment target image and a standard image, and the brainwave analysis unit acquires a brainwave feature amount on the basis of a change in a brainwave in accordance with a display period of the images.

(17)

An information processing method executed in an information processing device including:

a brainwave analysis step of measuring a brainwave of a subject to which a stimulus is presented and calculating a brainwave feature amount by a brainwave analysis unit;

a subjective assessment analysis step of acquiring a subjective assessment value with respect to the stimulus of the subject by a subjective assessment analysis unit; and a model construction step of constructing an assessment model representing relevance between the brainwave feature amount and the subjective assessment value by a model construction unit.

(18)

An information processing method executed in an information processing device including:

a brainwave analysis step of measuring a brainwave of a subject to which a stimulus is presented and calculating a brainwave feature amount by a brainwave analysis unit, in which a stimulus determination unit executes a stimulus determination step of applying an assessment model for enabling a subjective assessment value based on the brainwave feature amount to be acquired to estimate the subjective assessment value from the brainwave feature amount of the subject.

(19)

A program causing an information processing device to execute information processing, the program including:

a stimulus presentation step of presenting a stimulus to a subject in a stimulus presentation unit;

a brainwave analysis step of measuring a brainwave of a subject to which a stimulus is presented and calculating a brainwave feature amount in a brainwave analysis unit;

a subjective assessment analysis step of acquiring a subjective assessment value with respect to the stimulus of the subject in a subjective assessment analysis unit; and a model construction step of constructing an assessment model representing relevance between the brainwave feature amount and the subjective assessment value in a model construction unit.

(20)

A program causing an information processing device to execute information processing, the program including:

a brainwave analysis step of measuring a brainwave of a subject to which a stimulus is presented and calculating a brainwave feature amount in a brainwave analysis unit; and a stimulus determination step of applying an assessment model for enabling a subjective assessment value based on the brainwave feature amount to be acquired to estimate the subjective assessment value from the brainwave feature amount of the subject in a stimulus determination unit executes.

In addition, the series of processes described in this specification can be executed by hardware, software, or a combination configuration of the hardware and the software. In a case in which a process is executed by software, a program that records a process sequence can be installed in a memory of a computer embedded in dedicated hardware to be executed or a program can be installed in a general-purpose computer capable of executing various processes to be executed. For example, the program can be recorded in advance on a recording medium. In addition to the installation on a computer from a recording medium, the program can also be received via a network such as a Local Area Network (LAN) or the Internet and can be installed on a recording medium such as a built-in hard disk.

Also, various processes described in this specification may be executed chronologically as described above and may also be executed in parallel or individually according to a processing capability of a device executing the processes or as necessary. Note that in this specification, the term "system" refers to a logical aggregate configuration of multiple devices, and the respective devices of the configuration are not limited to being inside the same housing.

INDUSTRIAL APPLICABILITY

As described above, according to a configuration of an embodiment of the present disclosure, it is possible to realize a configuration capable of constructing an assessment model for enabling a subjective assessment value to be estimated from a brainwave feature amount and acquiring assessment data which does not deviate from a subjective assessment result on the basis of an objective brainwave signal by using the assessment model.

Specifically, an assessment model representing relevance between a brainwave feature amount of a subject and a subjective assessment value of the subject with respect to a stimulus is constructed by presenting the stimulus to the subject. For example, images with different image qualities and a standard image are alternately displayed on a display unit which is a stimulus presentation unit, brainwave feature amount corresponding to an image quality of a subject observing the displayed images and subjective assessment values corresponding to image qualities are acquired, and an image quality assessment model for enabling subjective assessment values to be estimated from the brainwave feature amounts is constructed by machine learning in which the brainwave feature amounts and the subjective assessment values are used as input data.

In this configuration, it is possible to construct an assessment model for enabling subjective assessment values to be estimated from brainwave feature amounts and realize a configuration capable of acquiring assessment data which does not deviate from the subjective assessment result on the basis of objective brainwave signals by using the assessment model.

REFERENCE SIGNS LIST 100 assessment model construction device
101 stimulus presentation unit
121 brainwave measurement unit
122 brainwave recording unit
123 brainwave analysis unit
131 subjective assessment acquisition unit
132 subjective assessment recording unit
133 subjective assessment analysis unit
141 result integration unit
150 model construction unit
180 subject
201 storage unit
202 learning data input unit
203 machine learning execution unit
204 assessment model storage unit
211 test data input unit
212 assessment model verification unit
213 assessment model output unit
220 image quality assessment model
301 stimulus presentation unit
321 brainwave measurement unit
322 brainwave recording unit
323 brainwave analysis unit
351 assessment model storage unit
352 stimulus determination unit
353 result (image quality assessment result) output unit
501 CPU
502 ROM
503 RAM
504 bus
505 input and output interface
506 input unit
507 output unit
508 storage unit
509 communication unit
510 drive
511 removable medium

The invention claimed is:

1. An information processing device, comprising:
   central processing unit (CPU) configured to:
   measure a brainwave of a subject to which a stimulus is presented;
   calculate a brainwave feature amount based on the brainwave of the subject;
   acquire a subjective assessment value with respect to the stimulus of the subject; and
   construct an assessment model through machine learning based on input data as learning data, wherein
   the brainwave feature amount and the subjective assessment value are the input data, and
   the assessment model represents relevance between the brainwave feature amount and the subjective assessment value.

2. The information processing device according to claim 1, wherein the CPU is further configured to:
   acquire a plurality of brainwave feature amounts corresponding to a plurality of image qualities obtained by a presentation of a plurality of images with different image qualities to the subject; and
   acquire a plurality of subjective assessment values corresponding to the plurality of image qualities.

3. The information processing device according to claim 1, wherein the CPU is further configured to:
   execute supervised machine learning based on the brainwave feature amount as student data and the subjective assessment value as supervisor data.

4. The information processing device according to claim 1, wherein the CPU is further configured to execute the machine learning in which a support vector machine (SVM) is applied as a machine learning algorithm.

5. The information processing device according to claim 2, wherein the plurality of images has different dynamic range.

6. The information processing device according to claim 1, wherein the CPU is further configured to:
   execute the presentation of the stimulus as alternate presentation of an assessment target image and a standard image; and
   acquire the brainwave feature amount based on a change in the brainwave based on a display period of a plurality of images.

7. The information processing device according to claim 1, wherein the CPU is further configured to:
   acquire steady-state visual evoked potential (SSVEP) from the brainwave of the subject; and
   calculate the brainwave feature amount based on the SSVEP.

8. The information processing device according to claim 7, wherein the CPU is further configured to:
   execute the presentation of the stimulus as alternate presentation of an assessment target image and a standard image; and
   analyze intensity of the SSVEP of the subject based on a display period of a plurality of images.

9. The information processing device according to claim 1, wherein the CPU is further configured to acquire the subjective assessment value of the subject based on a mean opinion score (MOS) scheme.

10. The information processing device according to claim 1, wherein the CPU is further configured to construct the assessment model to estimate the subjective assessment value from the brainwave feature amount.

11. The information processing device according to claim 10, wherein the CPU is further configured to:
- calculate a plurality of different brainwave feature amounts and
- construct the assessment model to estimate the subjective assessment value from the plurality of different brainwave feature amounts.

12. An information processing device, comprising: a CPU configured to:
- measure a brainwave of a subject to which a stimulus is presented;
- calculate a brainwave feature amount based on the brainwave of the subject;
- control a storage device to store an assessment model to enable a subjective assessment value based on the brainwave feature amount, wherein
  - the assessment model is an image quality assessment model generated based on supervised machine learning, and
  - the subjective assessment value is supervisor data and the brainwave feature amount is student data; and
- estimate the subjective assessment value from the brainwave feature amount of the subject based on the assessment model.

13. The information processing device according to claim 12, wherein
- the assessment model represents a correspondence relation between a plurality of brainwave feature amounts corresponding to a plurality of image qualities and a plurality of subjective assessment values corresponding to the plurality of image qualities, and
- the plurality of image qualities is based on a presentation of a plurality of images with different image qualities to the subject.

14. The information processing device according to claim 12, wherein the CPU is further configured to:
- execute the presentation of the stimulus as alternate presentation of an assessment target image and a standard image; and
- acquire the brainwave feature amount based on a change in the brainwave based on a display period of a plurality of images.

15. An information processing method comprising:
- measuring a brainwave of a subject to which a stimulus is presented;
- calculating a brainwave feature amount based on the brainwave of the subject;
- acquiring a subjective assessment value with respect to the stimulus of the subject; and
- constructing an assessment model through machine learning based on input data as learning data, wherein
  - the brainwave feature amount and the subjective assessment value are the input data, and
  - the assessment model represents relevance between the brainwave feature amount and the subjective assessment value.

16. An information processing method comprising:
- measuring a brainwave of a subject to which a stimulus is presented;
- calculating a brainwave feature amount based on the brainwave of the subject;
- applying an assessment model to enable a subjective assessment value based on the brainwave feature amount, wherein
  - the assessment model is an image quality assessment model generated based on supervised machine learning, and
  - the subjective assessment value is supervisor data and the brainwave feature amount is student data; and
- estimating the subjective assessment value from the brainwave feature amount of the subject based on the assessment model.

17. A non-transitory computer-readable medium having stored thereon computer-executable instructions that, when executed by a processor, cause the processor to execute operations, the operations comprising:
- measuring a brainwave of a subject to which a stimulus is presented;
- calculating a brainwave feature amount based on the brainwave of the subject;
- acquiring a subjective assessment value with respect to the stimulus of the subject; and
- constructing an assessment model through machine learning based on input data as learning data, wherein
  - the brainwave feature amount and the subjective assessment value are the input data; and
  - the assessment model represents relevance between the brainwave feature amount and the subjective assessment value.

18. A non-transitory computer-readable medium having stored thereon computer-executable instructions that, when executed by a processor, cause the processor to execute operations, the operations comprising:
- measuring a brainwave of a subject to which a stimulus is presented;
- calculating a brainwave feature amount based on the brainwave of the subject;
- applying an assessment model to enable a subjective assessment value based on the brainwave feature amount, wherein
  - the assessment model is an image quality assessment model generated based on supervised machine learning, and
  - the subjective assessment value is supervisor data and the brainwave feature amount is student data; and
- estimating the subjective assessment value from the brainwave feature amount of the subject based on the assessment model.

* * * * *